US010906937B2

(12) United States Patent
Pinhasov et al.

(10) Patent No.: US 10,906,937 B2
(45) **Date of Patent: *Feb. 2, 2021**

(54) PEPTIDES AND COMPOSITIONS COMPRISING SAME AND USES THEREOF IN THE TREATMENT OF DISEASES

(71) Applicant: Ariel-University Research and Development Company Ltd., Ariel (IL)

(72) Inventors: Albert Pinhasov, Etz Ephraim (IL); Osnat Ashur-Fabian, Tzur-Moshe (IL)

(73) Assignee: Ariel-University Research and Development Company Ltd., Ariel (IL)

( * ) Notice: Subject to any disclaimer, the term of this patent is extended or adjusted under 35 U.S.C. 154(b) by 0 days.

This patent is subject to a terminal disclaimer.

(21) Appl. No.: 16/299,206

(22) Filed: Mar. 12, 2019

(65) Prior Publication Data

US 2019/0194253 A1 Jun. 27, 2019

Related U.S. Application Data

(63) Continuation of application No. 15/554,719, filed as application No. PCT/IL2016/050243 on Mar. 3, 2016, now Pat. No. 10,266,567.

(60) Provisional application No. 62/127,854, filed on Mar. 4, 2015.

(51) Int. Cl.

| | |
|---|---|
| ***A61K 38/08*** | (2019.01) |
| ***C07K 7/06*** | (2006.01) |
| ***A61K 38/12*** | (2006.01) |
| *A61K 38/00* | (2006.01) |

(52) U.S. Cl.

CPC ................ *C07K 7/06* (2013.01); *A61K 38/08* (2013.01); *A61K 38/12* (2013.01); *A61K 38/00* (2013.01)

(58) Field of Classification Search

CPC ................................. A61K 38/08; C07K 7/06

See application file for complete search history.

(56) References Cited

U.S. PATENT DOCUMENTS

| | | | | |
|---|---|---|---|---|
| 5,767,071 | A | 6/1998 | Palladino et al. | |
| 7,192,754 | B2 | 3/2007 | Kamimura et al. | |
| 7,332,310 | B2 | 2/2008 | Nakagawa et al. | |
| 10,266,567 | B2 * | 4/2019 | Pinhasov | C07K 7/06 |
| 2012/0301968 | A1 | 11/2012 | Naito et al. | |
| 2014/0178950 | A1 | 6/2014 | Franklin et al. | |
| 2017/0037426 | A1 * | 2/2017 | Alexandrov | C07K 14/415 |
| 2018/0072771 | A1 | 3/2018 | Pinhasov et al. | |

FOREIGN PATENT DOCUMENTS

| | | |
|---|---|---|
| CN | 103044522 | 4/2013 |
| EP | 2345737 | 7/2011 |
| KR | 10-2013-0064710 | 6/2013 |
| WO | WO 2016/139667 | 9/2016 |
| WO | WO 2019/198090 | 10/2019 |

OTHER PUBLICATIONS

Translation of KR 20130064710 (Jun. 18, 2013). (Year: 2013).*
"Determination of the Cysteine and Cystine Content of Proteins by Amino Acid Analysis: Application to the Characterization of Disulfide-Coupled Folding Intermediates", Journal of Protein Chemistry, 17(1): 37-43, 1998, by Thannhauser et al.
International Preliminary Report on Patentability dated Sep. 14, 2017 From the International Bureau of WIPO Re. Application No. PCT/IL2016/050243. (19 Pages).
International Search Report and the Written Opinion dated May 19, 2016 From the International Searching Authority Re. Application No. PCT/IL2016/050243.
Official Action dated Jul. 19, 2018 From the US Patent and Trademark Office Re. U.S. Appl. No. 15/554,719. (17 pages).
Supplementary European Search Report and the European Search Opinion dated Feb. 8, 2019 From the European Patent Office Re. Application No. 16758561.1. (15 Pages).
Supplementary Partial European Search Report and the European Provisional Opinion [Communication Pursuant to Rule 164(1) EPC] dated Nov. 6, 2018 From the European Patent Office Re. Application No. 16758561.1. (19 Pages).
Benveniste et al. "Type I Interferons as Anti-Inflammatory Mediators", Science's STKE, 2007(416): pe70-1-pe70-4, Dec. 11, 2007.
Capasso et al. "RGDechi-hCit: AlphavBeta3 Selective Pro-Apoptotic Peptide as Potential Carrier for Drug Delivery Into Melanoma Metastatic Cells", PLOS ONE, 9(9): e106441-1-e106441-10, Sep. 23, 2014. Figs.5, 7-8.
Cazorla et al. "Cyclotraxin-B, the First Highly Potent and Selective TrkB Inhibitor, Has Anxiolytic Properties in Mice", PLoS ONE, XP055517106, 5(3): e9777-1-e9777-17, Published Online Mar. 19, 2010.
Cohen et al. "Abstract 17: Non-RGDBased Strategies to Target the Thyroid Hormone Receptor-integrin AvBeta3: Lessons From Myeloma Cells.", Abstracts of AACR Special Conference on Hematologic Malignancies: Translating Discoveries to Novel Therapies, Philadelphia, PA, USA, Sep. 20-23, 2014, Clinical Cancer Research, XP055515925, 21(17 Suppl.): # A17, Sep. 2015.
Francis "Selective Peptide to AlphavBeta3 Integrin for the Treatment of Melanoma", Ariel University R&D Company Ltd., Life Sciences and Biotechnology, p. 1-9, Dec. 28, 2014.
Franklin et al. "Sec ID No. 16042, Sequence Detail(s) For Application 14099704", 2 Pages, Jun. 26, 2014.

(Continued)

*Primary Examiner* — Jeffrey E. Russel

(57) ABSTRACT

Isolated peptides are disclosed. The peptide comprises an amino acid sequence selected from the group consisting of SEQ ID NOs: 1-5 and 11-15, with the proviso that the amino acid sequence does not consist of SEQ ID NO: 11, SEQ ID NO: 15 or SEQ ID NO: 1, wherein the peptide is no longer than 50 amino acids. Pharmaceutical compositions comprising same and uses thereof for treatment of diseases associated with serotonin transport and/or $\alpha V\beta 3$ activity are also disclosed.

13 Claims, 15 Drawing Sheets

Specification includes a Sequence Listing.

(56) References Cited

OTHER PUBLICATIONS

Liu et al. "Type I Interferons Promote the Survival and Proinflammatory Properties of Transitional B Cells in Systemic Lupus Erythematosus Patients", Cellular & Molecular Immunology, p. 1-13, Published Online Mar. 21, 2018.
Matsuda et al. "Brain-Derived Neurotrophic Factor Induces Migration of Endothelial Cells Through a TrkB-ERK-Integrin AlphavBeta3-FAK Cascade", Journal of Cellular Physiology, XP055517252, 227(5): 2123-2129, Published Online Jul. 18, 2011.
Nakagawa et al. "Seq ID No. 5036, Sequence Detail(s) for Application 10805394", 1 page, Feb. 19, 2008.
Ngubane et al. "High-Throughput Sequencing Enhanced Phage Display Identifies Peptides That Bind Myobacteria", PLOS ONE, 8(11): e77844-1-e77844-11, Nov. 12, 2013. Table 1.
Redko et al. "Toward the Development of a Novel Non-RGD Cyclic Peptide Drug Conjugate for Treatment of Human Metastatic Melanoma", Oncotarget, XP055515798, 8(1): 757-768, Published Online Oct. 19, 2016.
Rodgers et al. "Integrin AvBeta3 Binds a Unique Non-RGD Site Near the C-Terminus of Human Tropoelastin", Biochimie, XP055515938, 86(3): 173-178, Available Online Apr. 2, 2004.
Whyte et al. "Serotonin Transporter and Integrin Beta 3 Genes Interact to Modulate Serotonin Uptake in Mouse Brain", Neurochemistry International, 73: 122-126, Available Online Sep. 29, 2013.
Yakobovich et al. "Novel Synthetic Cyclic Integrin AvBeta3 Binding Peptide ALOS4: Antitumor Activity in Mouse Melanoma Models", Oncotarget, XP055515801, 7(39): 63549-63560, Published Online Aug. 18, 2016.
Zhong et al. "Mimotopes Selected With Neutralizing Antibodies Against Multiple Subtypes of Influenza A", Virology Journal, 8(542): 1-11, Dec. 15, 2011.
International Search Report and the Written Opinion dated Jul. 16, 2019 From the International Searching Authority Re. Application No. PCT/IL2019/050417. (13 Pages).

* cited by examiner

ALOS-1

ALOS-2

ALOS-3

ALOS-4
Fluorescence (log)
1000000
100000
10000
1000
1
10
100
Conc (Log)

SEQUENCE LISTING

```
<160> NUMBER OF SEQ ID NOS: 20

<210> SEQ ID NO 1
<211> LENGTH: 9
<212> TYPE: PRT
<213> ORGANISM: Artificial sequence
<220> FEATURE:
<223> OTHER INFORMATION: ALOS-1 oligopeptide

<400> SEQUENCE: 1

Cys Asn Leu Ser Ser Ser Trp Ile Cys
1               5


<210> SEQ ID NO 2
<211> LENGTH: 9
<212> TYPE: PRT
<213> ORGANISM: Artificial sequence
<220> FEATURE:
<223> OTHER INFORMATION: ALOS-2 oligopeptide

<400> SEQUENCE: 2

Cys Pro Pro Ser Asn His Leu Leu Cys
1               5


<210> SEQ ID NO 3
<211> LENGTH: 9
<212> TYPE: PRT
<213> ORGANISM: Artificial sequence
<220> FEATURE:
<223> OTHER INFORMATION: ALOS-3 oligopeptide

<400> SEQUENCE: 3

Cys Ala Pro Ser Pro Ser Arg Leu Cys
1               5


<210> SEQ ID NO 4
<211> LENGTH: 9
<212> TYPE: PRT
<213> ORGANISM: Artificial sequence
<220> FEATURE:
<223> OTHER INFORMATION: ALOS-3 oligopeptide

<400> SEQUENCE: 4

Cys Ser Ser Ala Gly Ser Leu Phe Cys
1               5


<210> SEQ ID NO 5
<211> LENGTH: 9
<212> TYPE: PRT
<213> ORGANISM: Artificial sequence
<220> FEATURE:
```

<223> OTHER INFORMATION: ALOS-5 oligopeptide

<400> SEQUENCE: 5

Cys Pro Leu His Ala Arg Leu Pro Cys
1               5

<210> SEQ ID NO 6
<211> LENGTH: 27
<212> TYPE: DNA
<213> ORGANISM: Artificial sequence
<220> FEATURE:
<223> OTHER INFORMATION: nucleic acids sequence encoding ALOS-1

<400> SEQUENCE: 6
tgtaatcttt cgtcttcatg gatttgc 27

<210> SEQ ID NO 7
<211> LENGTH: 27
<212> TYPE: DNA
<213> ORGANISM: Artificial sequence
<220> FEATURE:
<223> OTHER INFORMATION: nucleic acids sequence encoding ALOS-2

<400> SEQUENCE: 7
tgtccgccgt ctaatcatct gttgtgc 27

<210> SEQ ID NO 8
<211> LENGTH: 27
<212> TYPE: DNA
<213> ORGANISM: Artificial sequence
<220> FEATURE:
<223> OTHER INFORMATION: nucleic acids sequence encoding ALOS-3

<400> SEQUENCE: 8
tgtgctcctt ctccttctcg gctttgc 27

<210> SEQ ID NO 9
<211> LENGTH: 27
<212> TYPE: DNA
<213> ORGANISM: Artificial sequence
<220> FEATURE:
<223> OTHER INFORMATION: nucleic acids sequence encoding ALOS-4

<400> SEQUENCE: 9
tgttcttctg ctggttctct tttttgc 27

<210> SEQ ID NO 10
<211> LENGTH: 27
<212> TYPE: DNA
<213> ORGANISM: Artificial sequence
<220> FEATURE:
<223> OTHER INFORMATION: nucleic acids sequence encoding ALOS-5

<400> SEQUENCE: 10
tgtccgcttc atgcgcggct gccttgc 27

<210> SEQ ID NO 11
<211> LENGTH: 7
<212> TYPE: PRT
<213> ORGANISM: Artificial sequence
<220> FEATURE:
<223> OTHER INFORMATION: oligopeptide

<400> SEQUENCE: 11

Asn Leu Ser Ser Ser Trp Ile
1               5

-continued

<210> SEQ ID NO 12
<211> LENGTH: 7
<212> TYPE: PRT
<213> ORGANISM: Artificial sequence
<220> FEATURE:
<223> OTHER INFORMATION: oligopeptide

<400> SEQUENCE: 12

Pro Pro Ser Asn His Leu Leu
1 5

<210> SEQ ID NO 13
<211> LENGTH: 7
<212> TYPE: PRT
<213> ORGANISM: Artificial sequence
<220> FEATURE:
<223> OTHER INFORMATION: oligopeptide

<400> SEQUENCE: 13

Ala Pro Ser Pro Ser Arg Leu
1 5

<210> SEQ ID NO 14
<211> LENGTH: 7
<212> TYPE: PRT
<213> ORGANISM: Artificial sequence
<220> FEATURE:
<223> OTHER INFORMATION: oligopeptide

<400> SEQUENCE: 14

Ser Ser Ala Gly Ser Leu Phe
1 5

<210> SEQ ID NO 15
<211> LENGTH: 7
<212> TYPE: PRT
<213> ORGANISM: Artificial sequence
<220> FEATURE:
<223> OTHER INFORMATION: oligopeptide

<400> SEQUENCE: 15

Pro Leu His Ala Arg Leu Pro
1 5

<210> SEQ ID NO 16
<211> LENGTH: 21
<212> TYPE: DNA
<213> ORGANISM: Artificial sequence
<220> FEATURE:
<223> OTHER INFORMATION: oligonucleotide encoding peptide Seq ID 11

<400> SEQUENCE: 16
aatctttcgt cttcatggat t 21

<210> SEQ ID NO 17
<211> LENGTH: 21
<212> TYPE: DNA
<213> ORGANISM: Artificial sequence
<220> FEATURE:
<223> OTHER INFORMATION: oligonucleotide encoding peptide Seq ID 12

<400> SEQUENCE: 17
ccgccgtcta atcatctgtt g 21

<210> SEQ ID NO 18

-continued

```
<211> LENGTH: 21
<212> TYPE: DNA
<213> ORGANISM: Artificial sequence
<220> FEATURE:
<223> OTHER INFORMATION: oligonucleotide encoding peptide Seq ID 13

<400> SEQUENCE: 18

gctccttctc cttctcggct t                                              21


<210> SEQ ID NO 19
<211> LENGTH: 21
<212> TYPE: DNA
<213> ORGANISM: Artificial sequence
<220> FEATURE:
<223> OTHER INFORMATION: oligonucleotide encoding peptide Seq ID 14

<400> SEQUENCE: 19

tcttctgctg gttctctttt t                                              21


<210> SEQ ID NO 20
<211> LENGTH: 21
<212> TYPE: DNA
<213> ORGANISM: Artificial sequence
<220> FEATURE:
<223> OTHER INFORMATION: oligonucleotide encoding peptide Seq ID 15

<400> SEQUENCE: 20

ccgcttcatg cgcggctgcc t                                              21
```

PEPTIDES AND COMPOSITIONS COMPRISING SAME AND USES THEREOF IN THE TREATMENT OF DISEASES

RELATED APPLICATIONS

This application is a Continuation of U.S. patent application Ser. No. 15/554,719, which is the National Phase of PCT Patent Application No. PCT/IL2016/050243 having International filing date of Mar. 3, 2016, which claims the benefit of priority under 35 USC § 119(e) of U.S. Provisional Patent Application No. 62/127,854 filed on Mar. 4, 2015.

SEQUENCE LISTING STATEMENT

The ASCII file, entitled 76686SequenceListing.txt, created on Mar. 6, 2019, comprising 4,305 bytes, submitted concurrently with the filing of this application is incorporated herein by reference. The sequence listing submitted herewith is identical to the sequence listing forming part of the international application.

FIELD AND BACKGROUND OF THE INVENTION

The present invention, in some embodiments thereof, relates to peptide agents for the treatment of diseases.

Dysfunctions in serotonin (5-hydroxytryptamine, 5-HT) systems have been associated with several psychiatric illnesses, including anxiety, depression, obsessive-compulsive disorders and autism spectrum disorders. Several genetic variants in the 5-HT transporter gene (SERT, SLC6A4) have been associated with behavioral phenotypes manifested in these disorders, especially in the context of genetic interactions or under specific environmental conditions. Variations in whole blood 5-HT levels, found in several neuropsychiatric disorders, including autism, bipolar disorder and seasonal affective disorder are associated with non-coding variation in ITGB3. Genetic interaction of ITGB3, which encodes the integrin b3 subunit (forming the integrin αIIvbβ3 in platelets and integrin αvβ3 in brain), and SLC6A4, either in mRNA expression or autism susceptibility, further reinforces the suggestion that these two genes interact to modify 5-HT homeostasis. Whyte et al. demonstrates that ITGB3 and SLC6A4 interact to modulate SERT expression and function in the brain (Whyte et al. Neurochemistry International 73 (2014) 122-126).

Background art includes Zhong et al. Virology Journal 2011, 8:542 and European Patent Application EP 2345737 A1.

SUMMARY OF THE INVENTION

According to an aspect of some embodiments of the present invention there is provided an isolated peptide comprising an amino acid sequence selected from the group consisting of SEQ ID NOs: 1-5 and 11-15, with the proviso that the amino acid sequence does not consist of SEQ ID NO: 11, SEQ ID NO: 15 or SEQ ID NO: 1, wherein the peptide is no longer than 50 amino acids.

According to an aspect of some embodiments of the present invention there is provided an isolated peptide consisting of an amino acid sequence selected from the group consisting of 2-5 and 12-14.

According to an aspect of some embodiments of the present invention there is provided a composition of matter comprising an isolated peptide which comprises an amino acid sequence selected from the group consisting of SEQ ID NOs: 11-15, wherein the peptide is attached to a therapeutic moiety or a detectable moiety.

According to an aspect of some embodiments of the present invention there is provided a pharmaceutical composition comprising as the active agent a peptide of any one of the peptides disclosed or the composition of matter disclosed, and a pharmaceutically acceptable carrier.

According to an aspect of some embodiments of the present invention there is provided a method of treating a disease or condition associated with serotonin transport in a subject in need thereof, the method comprising administering to the subject a therapeutically effective amount of a peptide comprising an amino acid sequence selected from the group consisting of SEQ ID NOs: 11-15, thereby treating the disease.

According to an aspect of some embodiments of the present invention there is provided a method of treating a disease or condition associated with αVβ3 activity in a subject in need thereof, the method comprising administering to the subject a therapeutically effective amount of a peptide comprising an amino acid sequence selected from the group consisting of SEQ ID NOs: 11-15, thereby treating the disease.

According to an aspect of some embodiments of the present invention there is provided a method of treating cancer or anxiety in a subject in need thereof, comprising administering to the subject a therapeutically effective amount of a peptide comprising an amino acid sequence selected from the group consisting of SEQ ID NOs: 11-15, thereby treating the cancer or anxiety.

According to some embodiments of the invention, the peptide is capable of binding to αVβ3 integrin.

According to some embodiments of the invention, the peptide is cyclic.

According to some embodiments of the invention, the N terminus of the peptide is bound to the C terminus of the peptide.

According to some embodiments of the invention, the N terminal amino acid and the C terminal amino acids are cysteines.

According to some embodiments of the invention, the isolated peptide comprises the sequence selected from the group as set forth in SEQ ID NOs: 2-4.

According to some embodiments of the invention, the isolated peptide consists of the sequence selected from the group as set forth in SEQ ID NOs: 2-4.

According to some embodiments of the invention, the isolated peptide consists of the amino acid sequence selected from the group consisting of SEQ ID NOs: 12-14.

According to some embodiments of the invention, the isolated peptide is no more than 20 amino acids in length.

According to some embodiments of the invention, the isolated peptide is no more than 10 amino acids in length.

According to some embodiments of the invention, the peptide comprises an amino acid sequence selected from the group consisting of SEQ ID NOs: 12-14.

According to some embodiments of the invention, the peptide is cyclic.

According to some embodiments of the invention, the peptide is capable of binding to αVβ3 integrin.

According to some embodiments of the invention, the N terminus of the peptide is bound to the C terminus of the peptide.

According to some embodiments of the invention, the N terminal amino acid and the C terminal amino acids are cysteines.

According to some embodiments of the invention, the peptide is no more than 20 amino acids in length.

According to some embodiments of the invention, the peptide is no more than 10 amino acids in length.

According to some embodiments of the invention, the disease or condition is a behavioral disease or condition.

According to some embodiments of the invention, the disease is cancer.

According to some embodiments of the invention, the cancer is a metastasized cancer.

According to some embodiments of the invention, the cancer is selected from the group consisting of melanoma, ovarian cancer and cervical cancer.

According to some embodiments of the invention, the behavioral disease or condition is selected from the group consisting of depression, anxiety, phobia, addiction, aggressiveness, impulsiveness, panic, eating, sleep and psychotic disorder and obsessive-compulsive and female sexual dysfunctions.

According to some embodiments of the invention, the peptides comprise the sequence selected from the group as set forth in SEQ ID NOs: 1-5.

According to some embodiments of the invention, the peptides consist of the sequence selected from the group as set forth in SEQ ID NOs: 1-5.

According to some embodiments of the invention, the peptides consist of the sequence selected from the group as set forth in SEQ ID NOs: 11-15.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

Some embodiments of the invention are herein described, by way of example only, with reference to the accompanying drawings and images. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings.

DESCRIPTION OF SPECIFIC EMBODIMENTS OF THE INVENTION

The present invention, in some embodiments thereof, relates to peptide agents for the treatment of diseases.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

Dysfunctions in serotonin (5-hydroxytryptamine, 5-HT) systems have been associated with several psychiatric illnesses, including anxiety, depression, obsessive-compulsive disorders and autism spectrum disorders.

It was recently discovered that integrin αvβ3 modulates serotonin transport.

Accordingly, the present inventors searching for new agents capable of modulating serotonin, screened a large number of peptides that bind to integrin αvβ3 using a phage display platform. Of the myriad of peptides that were screened using the assay, only 5 were shown to bind specifically to the integrin αvβ3 receptor.

Figure 3:
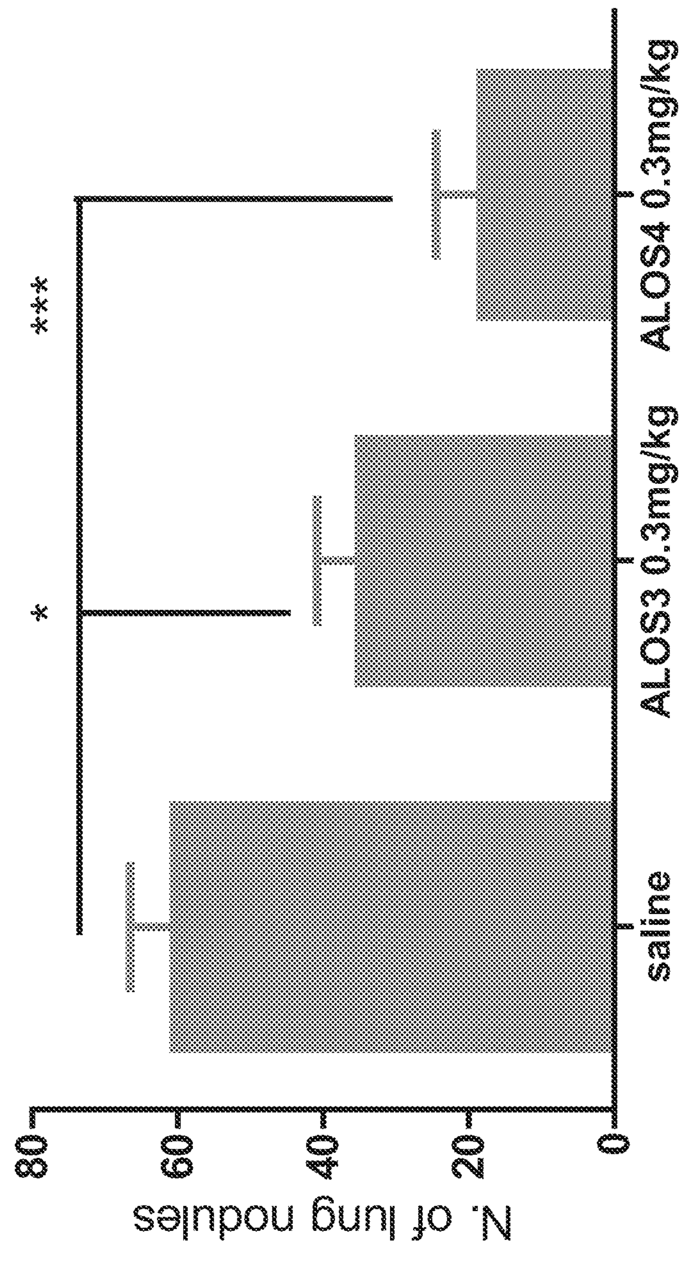
FIG. 3 is a graph illustrating the total number of visible nodules on the lung of saline and ALOS3 and ALOS4 treated mice. Statistical analysis was performed using one-way ANOVA, followed by Bonferroni post-hoc correction.
Figure 4:
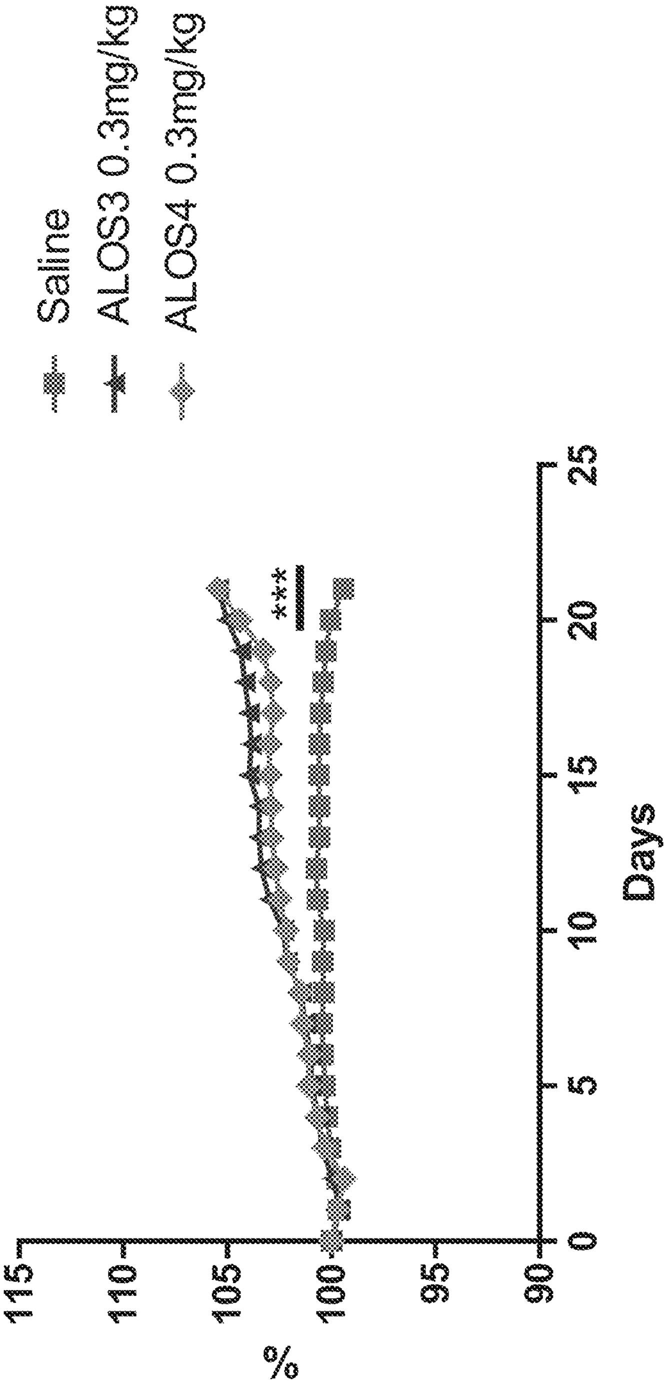
FIG. 4 is a graph illustrating the effect of ALOS3 and ALOS4 on animals' weight. Animals' weight is presented as percent compared to entry point (Baseline) calculated for each individual animal. Statistical difference was calculated using two-way ANOVA followed by Bonferroni post hoc correction.
Figure 5:
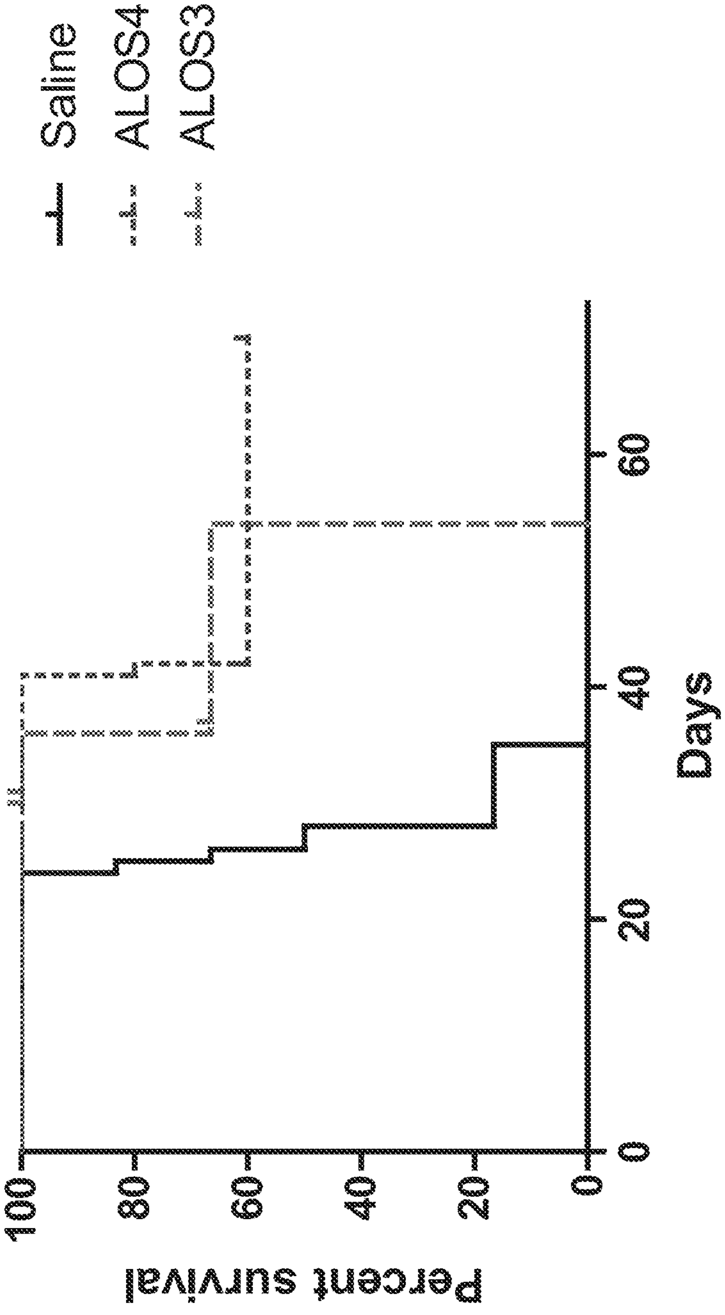
FIG. 5 is a graph illustrating that daily (5 days a week) ALOS3 (n=5) and ALOS4 (n=5) administration significantly delayed animals' death caused by melanoma cells metastasis compare to control (n=6). 5000 cells of B16-F10/0.2 ml/mouse were injected into the tail vein of 8 weeks old C57BL/6 mice.
Figure 6:
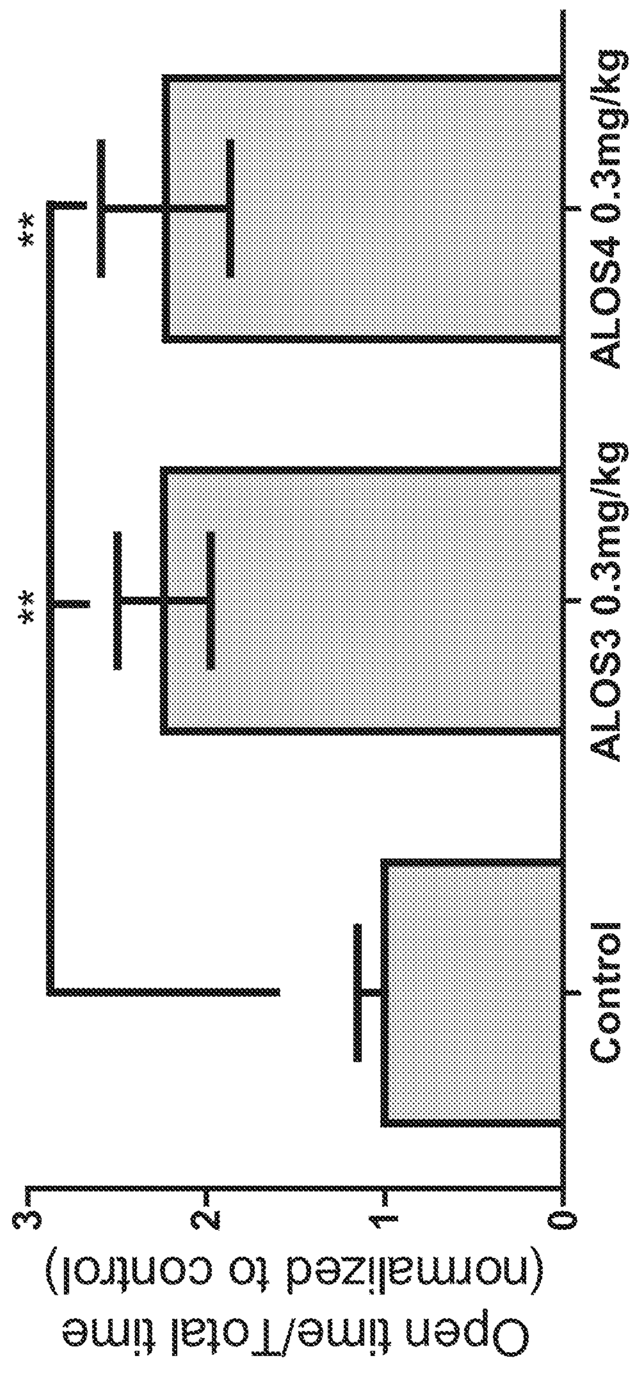
FIG. 6 is a graph illustrating the effect of ALOS3 and ALOS4 on animals performance in Elevated Plus Maze (EPM) test. Statistical difference was calculated using two-way ANOVA followed by Bonferroni post hoc test. ALOS3 and ALOS4 (0.3 mg/kg) exerted anxiolytic effect upon mice as measured by the ratio of time spent in open arms of the maze to total time. The statistical significance was assessed using two-way ANOVA followed by Bonferroni post hoc test indicated by (**) at $p<0.01$.

When analyzed for their ability to affect anxiety in cancer-bearing mice using an Elevated Plus Maze (EPM) test, the present inventors surprisingly found that not only did the peptide agents lower anxiety levels in the mice (FIG. 6), but also significantly reduced tumor size and metastasis of melanoma-affected mice (FIG. 3), prolonged the life-span of melanoma-affected mice (FIG. 5) and also reduced weight loss in these mice (FIG. 4). Further in vitro results show that these peptides also have a positive effect on cervical and ovarian cancer cell lines (FIGS. 1A-C and 2A-C).

Accordingly, the present inventors propose that the peptides may be used advantageously both for the treatment of cancer and behavioral diseases known to be related to serotonin transport and/or αvβ3 activity.

Thus, according to an aspect of the present invention there is provided a method of treating a disease or condition associated with serotonin transport in a subject in need thereof, the method comprising administering to the subject a therapeutically effective amount of a peptide comprising an amino acid sequence selected from the group consisting of SEQ ID NOs: 11-15, thereby treating the disease.

Diseases or conditions associated with serotonin transport include both behavioral diseases and conditions.

According to another aspect of the present invention there is provided a method of treating a disease or condition associated with αvβ3 in a subject in need thereof, the method comprising administering to the subject a therapeutically effective amount of a peptide comprising an amino acid sequence selected from the group consisting of SEQ ID NOs: 11-15, thereby treating the disease.

Diseases or conditions associated with αvβ3 binding include but are not limited to cancerous diseases.

Exemplary behavioral diseases and conditions include, but are not limited to depression, anxiety, phobias, panic, addictions, aggressiveness, impulsiveness, eating disorders, sleep disorders, obsessive-compulsive disorder, psychotic disorders, disorders involving the heat regulation mechanism, female sexual dysfunctions, which encompass hypoactive sexual desire disorder, sexual aversion disorder, female sexual excitation disorder, and the loss, inhibition or absence of sexual desire.

The term "cancer" as used herein refers to proliferative diseases including but not limited to carcinoma, lymphoma, blastoma, sarcoma, and leukemia. Particular examples of cancerous diseases but are not limited to: Myeloid leukemia such as Chronic myelogenous leukemia. Acute myelogenous leukemia with maturation. Acute promyelocytic leukemia, Acute nonlymphocytic leukemia with increased basophils, Acute monocytic leukemia. Acute myelomonocytic leukemia with eosinophilia; Malignant lymphoma, such as Birkitt's Non-Hodgkin's; Lymphocytic leukemia, such as Acute lymphoblastic leukemia. Chronic lymphocytic leukemia; Myeloproliferative diseases, such as Solid tumors Benign Meningioma, Mixed tumors of salivary gland, Colonic adenomas; Adenocarcinomas, such as Small cell lung cancer, Kidney, Uterus, Prostate, Bladder, Ovary, Colon, Sarcomas, Liposarcoma, myxoid, Synovial sarcoma, Rhabdomyosarcoma (alveolar), Extraskeletal myxoid chondrosarcoma, Ewing's tumor; other include Testicular and ovarian dysgerminoma, Retinoblastoma, Wilms' tumor, Neuroblastoma, Malignant melanoma, Mesothelioma, breast, skin, prostate, and ovarian.

According to a particular embodiment, the cancer is colorectal cancer, lung cancer, skin cancer, breast cancer, renal cancer, bone cancer, ovarian cancer, gastric cancer, bladder cancer, liver cancer, cervical cancer, fallopian cancer, brain tumor e.g. glioblastoma, leukemia, including acute myeloid leukemia and lymphoma.

According to a particular embodiment, the cancer is selected from the group consisting of ovarian cancer, cervical cancer and melanoma.

According to an embodiment, the cancer is melanoma.

Other disorders associated with αVβ3 activity include, but are not limited to osteoporosis, Paget's disease, ovariectomy-induced physiological change, rheumatic arthritis, osteoarthritis and angiogenesis-related eye disease, including but not limited to, age-related macular degeneration, diabetic retinopathy, corneal neovascularizing diseases, ischaemia-induced neovascularizing retinopathy, high myopia and retinopathy of prematurity.

As mentioned, in some embodiments, the peptides are capable of binding to αVβ3 integrin. According to one embodiment, the peptides bind in vitro to αVβ3 integrin. According to another embodiment, the peptides bind in vivo to αVβ3 integrin. This protein is a type of integrin that is a receptor for vitronectin. It consists of two components, integrin alpha V (CD51 ref seq NM_002210.4) and integrin beta 3 (CD61, ref seq NM_000212).

The peptides disclosed herein, may be capable of binding other integrins such as αVβ5 integrin and/or α5β1 integrin.

Binding affinity can be measured by any assay known or available to those skilled in the art, including but not limited to BIAcore measurements, ELISA assays, competition assays, etc. Bioactivity can be measured in vivo or in vitro by any assay known or available to those skilled in the art.

According to one embodiment, binding is measured using an antibody which is capable of specifically recognizing the peptides disclosed herein.

According to another embodiment, the binding is measured using peptides which are attached to a detectable moiety, wherein the αVβ3 integrin is immobilized onto a solid support.

Preferably, the peptide binds (e.g. in vitro) to the αVβ3 integrin with a Kd of at least 10 uM-100 nM.

According to another embodiment, the peptides do not bind to the RGD binding site of αVβ3 integrin.

According to still another embodiment, the peptides bind with at least 2 fold, at least 5 fold, at least 10 fold or at least 20 fold higher affinity to αVβ3 than α11bβ3 and/or α5β1 integrin.

The peptides described herein may comprise at least one of the following sequences: NLSSSWI (SEQ ID NO: 11), PPSNHLL (SEQ ID NO: 12), APSPSRL (SEQ ID NO: 13), SSAGSLF (SEQ ID NO: 14) or PLHARLP (SEQ ID NO: 15).

According to another embodiment, the peptides of this aspect of the present invention consist of at least one of the following sequences: NLSSSWI (SEQ ID NO: 11), PPSNHLL (SEQ ID NO: 12), APSPSRL (SEQ ID NO: 13), SSAGSLF (SEQ ID NO: 14) or PLHARLP (SEQ ID NO: 15).

The peptides described herein are at least 7 amino acids in length. Longer peptides are also contemplated by the inventors. Thus, the peptides may be 8 amino acids, 9 amino acids, 10 amino acids, 11 amino acids, 12 amino acids, 13 amino acids, 14 amino acids, 15 amino acids, 16 amino acids, 17 amino acids, 18 amino acids, 19 amino acids or 20 amino acids.

According to one embodiment, the peptides are not longer than 20 amino acids, 30 amino acids, 40 amino acids or 50 amino acids.

According to a particular embodiment the peptides are 9 amino acids, wherein each of the peptide sequences provided herein above are flanked by cysteine residues.

Accordingly, the peptides may comprise any of the following sequences: CNLSSSWIC (SEQ ID NO: 1), CPPSNHLLC (SEQ ID NO: 2), CAPSPSRLC (SEQ ID NO: 3), CSSAGSLFC (SEQ ID NO: 4) or CPLHARLPC (SEQ ID NO: 5).

According to another embodiment, the peptides consist of any of the following sequences: CNLSSSWIC (SEQ ID NO: 1), CPPSNHLLC (SEQ ID NO: 2), CAPSPSRLC (SEQ ID NO: 3), CSSAGSLFC (SEQ ID NO: 4) or CPLHARLPC (SEQ ID NO: 5).

The term "peptide" as used herein refers to a polymer of natural or synthetic amino acids, encompassing native peptides (either degradation products, synthetically synthesized peptides or recombinant peptides) and peptidomimetics (typically, synthetically synthesized peptides), as well as peptoids and semipeptoids which are peptide analogs, which may have, for example, modifications rendering the peptides even more stable while in a body or more capable of penetrating into cells. The peptide is shorter (e.g. a fragment of) than a naturally-occurring, full length protein.

Such modifications include, but are not limited to N terminus modification, C terminus modification, peptide bond modification, including, but not limited to, CH2-NH, CH2-S, CH2-S═O, O═C—NH, CH2-O, CH2-CH2, S═C—NH, CH═CH or CF═CH, backbone modifications, and residue modification. Methods for preparing peptidomimetic compounds are well known in the art and are specified, for example, in Quantitative Drug Design, C. A. Ramsden Gd., Chapter 17.2, F. Choplin Pergamon Press (1992), which is incorporated by reference as if fully set forth herein. Further details in this respect are provided hereinunder.

Peptide bonds (—CO—NH—) within the peptide may be substituted, for example, by N-methylated bonds (—N(CH3)-CO—), ester bonds (—C(R)H—C—O—O—C(R)—N—), ketomethylen bonds (—CO—CH2-), α-aza bonds (—NH—N(R)—CO—), wherein R is any alkyl, e.g., methyl, carba bonds (—CH2-NH—), hydroxyethylene bonds (—CH(OH)—CH2-), thioamide bonds (—CS—NH—), olefinic double bonds (—CH═CH—), retro amide bonds (—NH—CO—), peptide derivatives (—N(R)—CH2-CO—), wherein R is the "normal" side chain, naturally presented on the carbon atom.

These modifications can occur at any of the bonds along the peptide chain and even at several (2-3) at the same time.

Natural aromatic amino acids, Trp, Tyr and Phe, may be substituted for synthetic non-natural acid such as Phenylglycine, TIC, naphthylelanine (Nol), ring-methylated derivatives of Phe, halogenated derivatives of Phe or o-methyl-Tyr.

In addition to the above, the peptides of the present invention may also include one or more modified amino acids or one or more non-amino acid monomers (e.g. fatty acids, complex carbohydrates etc).

As used herein in the specification and in the claims section below the term "amino acid" or "amino acids" is understood to include the 20 naturally occurring amino acids; those amino acids often modified post-translationally in vivo, including, for example, hydroxyproline, phosphoserine and phosphothreonine; and other unusual amino acids including, but not limited to, 2-aminoadipic acid, hydroxylysine, isodemosine, nor-valine, nor-leucine and ornithine. Furthermore, the term "amino acid" includes both D- and L-amino acids (stereoisomers).

Tables 1 and 2 below list naturally occurring amino acids (Table 1) and non-conventional or modified amino acids (Table 2) which can be used with the present invention.

TABLE 1

| Amino Acid | Three-Letter Abbreviation | One-letter Symbol |
|---|---|---|
| alanine | Ala | A |
| Arginine | Arg | R |

TABLE 1-continued

| Amino Acid | Three-Letter Abbreviation | One-letter Symbol |
|---|---|---|
| Asparagine | Asn | N |
| Aspartic acid | Asp | D |
| Cysteine | Cys | C |
| Glutamine | Gln | Q |
| Glutamic Acid | Glu | E |
| glycine | Gly | G |
| Histidine | His | H |
| isoleucine | lie | I |
| leucine | Leu | L |
| Lysine | Lys | K |

TABLE 1-continued

| Amino Acid | Three-Letter Abbreviation | One-letter Symbol |
|---|---|---|
| Methionine | Met | M |
| phenylalanine | Phe | F |
| Proline | Pro | P |
| Serine | Ser | S |
| Threonine | Thr | T |
| tryptophan | Trp | W |
| tyrosine | Tyr | Y |
| Valine | Val | V |
| Any amino acid as above | Xaa | X |

TABLE 2

| Non-conventional amino acid | Code | Non-conventional amino acid | Code |
|---|---|---|---|
| α-aminobutyric acid | Abu | L-N-methylalanine | Nmala |
| α-amino-α-methylbutyrate | Mgabu | L-N-methylarginine | Nmarg |
| aminocyclopropane-carboxylate | Cpro | L-N-methylasparagine | Nmasn |
| | | L-N-methylaspartic acid | Nmasp |
| aminoisobutyric acid | Aib | L-N-methylcysteine | Nmcys |
| aminonorbornyl-carboxylate | Norb | L-N-methylglutamine | Nmgin |
| | | L-N-methylglutamic acid | Nmglu |
| cyclohexylalanine | Chexa | L-N-methylhistidine | Nmhis |
| cyclopentylalanine | Cpen | L-N-methylisolleucine | Nmile |
| D-alanine | Dal | L-N-methylleucine | Nmleu |
| D-arginine | Darg | L-N-methyllysine | Nmlys |
| D-aspartic acid | Dasp | L-N-methylmethionine | Nmmet |
| D-cysteine | Dcys | L-N-methylnorleucine | Nmnle |
| D-glutamine | Dgln | L-N-methylnorvaline | Nmnva |
| D-glutamic acid | Dglu | L-N-methylornithine | Nmorn |
| D-histidine | Dhis | L-N-methylphenylalanine | Nmphe |
| D-isoleucine | Dile | L-N-methylproline | Nmpro |
| D-leucine | Dleu | L-N-methylserine | Nmser |
| D-lysine | Dlys | L-N-methylthreonine | Nmthr |
| D-methionine | Dmet | L-N-methyltryptophan | Nmtrp |
| D-ornithine | Dorn | L-N-methyltyrosine | Nmtyr |
| D-phenylalanine | Dphe | L-N-methylvaline | Nmval |
| D-proline | Dpro | L-N-methylethylglycine | Nmetg |
| D-serine | Dser | L-N-methyl-t-butylglycine | Nmtbug |
| D-threonine | Dthr | L-norleucine | Nle |
| D-tryptophan | Dtrp | L-norvaline | Nva |
| D-tyrosine | Dtyr | α-methyl-aminoisobutyrate | Maib |
| D-valine | Dval | α-methyl-γ-aminobutyrate | Mgabu |
| D-α-methylalanine | Dmala | α ethylcyclohexylalanine | Mchexa |
| D-α-methylarginine | Dmarg | α-methylcyclopentylalanine | Mcpen |
| D-α-methylasparagine | Dmasn | α-methyl-α-napthylalanine | Manap |
| D-α-methylaspartate | Dmasp | α-methylpenicillamine | Mpen |
| D-α-methylcysteine | Dmcys | N-(4-aminobutyl)glycine | Nglu |
| D-α-methylglutamine | Dmgln | N-(2-aminoethyl)glycine | Naeg |
| D-α-methylhistidine | Dmhis | N-(3-aminopropyl)glycine | Norn |
| D-α-methylisoleucine | Dmile | N-amino-α-methylbutyrate | Nmaabu |
| D-α-methylleucine | Dmleu | α-napthylalanine | Anap |
| D-α-methyllysine | Dmlys | N-benzylglycine | Nphe |
| D-α-methylmethionine | Dmmet | N-(2-carbamylethyl)glycine | Ngln |
| D-α-methylornithine | Dmorn | N-(carbamylmethyl)glycine | Nasn |
| D-α-methylphenylalanine | Dmphe | N-(2-carboxyethyl)glycine | Nglu |
| D-α-methylproline | Dmpro | N-(carboxymethyl)glycine | Nasp |
| D-α-methylserine | Dmser | N-cyclobutylglycine | Ncbut |
| D-α-methylthreonine | Dmthr | N-cycloheptylglycine | Nchep |
| D-α-methyltryptophan | Dmtrp | N-cyclohexylglycine | Nchex |
| D-α-methyltyrosine | Dmty | N-cyclodecylglycine | Ncdec |
| D-α-methylvaline | Dmval | N-cyclododeclglycine | Ncdod |
| D-α-methylalnine | Dnmala | N-cyclooctylglycine | Ncoct |
| D-α-methylarginine | Dnmarg | N-cyclopropylglycine | Ncpro |
| D-α-methylasparagine | Dnmasn | N-cycloundecylglycine | Ncund |
| D-α-methylasparatate | Dnmasp | N-(2,2-diphenylethyl)glycine | Nbhm |
| D-α-methylcysteine | Dnmcys | N-(3,3-diphenylpropyl)glycine | Nbhe |
| D-N-methylleucine | Dnmleu | N-(3-indolylyethyl) glycine | Nhtrp |
| D-N-methyllysine | Dnmlys | N-methyl-γ-aminobutyrate | Nmgabu |
| N-methylcyclohexylalanine | Nmchexa | D-N-methylmethionine | Dnmmet |
| D-N-methylornithine | Dnmorn | N-methylcyclopentylalanine | Nmcpen |
| N-methylglycine | Nala | D-N-methylphenylalanine | Dnmphe |
| N-methylaminoisobutyrate | Nmaib | D-N-methylproline | Dnmpro |
| N-(1-methylpropyl)glycine | Nile | D-N-methylserine | Dnmser |

TABLE 2-continued

| Non-conventional amino acid | Code | Non-conventional amino acid | Code |
|---|---|---|---|
| N-(2-methylpropyl)glycine | Nile | D-N-methylserine | Dnmser |
| N-(2-methylpropyl)glycine | Nleu | D-N-methylthreonine | Dnmthr |
| D-N-methyltryptophan | Dnmtrp | N-(1-methylethyl)glycine | Nva |
| D-N-methyltyrosine | Dnmtyr | N-methyla-napthylalanine | Nmanap |
| D-N-methylvaline | Dnmval | N-methylpenicillamine | Nmpen |
| γ-aminobutyric acid | Gabu | N-(p-hydroxyphenyl)glycine | Nhtyr |
| L-t-butylglycine | Tbug | N-(thiomethyl)glycine | Ncys |
| L-ethylglycine | Etg | penicillamine | Pen |
| L-homophenylalanine | Hphe | L-α-methylalanine | Mala |
| L-α-methylarginine | Marg | L-α-methylasparagine | Masn |
| L-α-methylaspartate | Masp | L-α-methyl-t-butylglycine | Mtbug |
| L-α-methylcysteine | Mcys | L-methylethylglycine | Metg |
| L-α thylglutamine | Mgln | L-α-methylglutamate | Mglu |
| L-α-methylhistidine | Mhis | L-α-methylhomo phenylalanine | Mhphe |
| L-α-methylisoleucine | Mile | N-(2-methylthioethyl)glycine | Nmet |
| D-N-methylglutamine | Dnmgln | N-(3-guanidinopropyl)glycine | Narg |
| D-N-methylglutamate | Dnmglu | N-(1-hydroxyethyl)glycine | Nthr |
| D-N-methylhistidine | Dnmhis | N-(hydroxyethyl)glycine | Nser |
| D-N-methylisoleucine | Dnmile | N-(imidazolylethyl)glycine | Nhis |
| D-N-methylleucine | Dnmleu | N-(3-indolylyethyl)glycine | Nhtrp |
| D-N-methyllysine | Dnmlys | N-methyl-γ-aminobutyrate | Nmgabu |
| N-methylcyclohexylalanine | Nmchexa | D-N-methylmethionine | Dnmmet |
| D-N-methylornithine | Dnmorn | N-methylcyclopentylalanine | Nmcpen |
| N-methylglycine | Nala | D-N-methylphenylalanine | Dnmphe |
| N-methylaminoisobutyrate | Nmaib | D-N-methylproline | Dnmpro |
| N-(1-methylpropyl)glycine | Nile | D-N-methylserine | Dnmser |
| N-(2-methylpropyl)glycine | Nleu | D-N-methylthreonine | Dnmthr |
| D-N-methyltryptophan | Dnmtrp | N-(1-methylethyl)glycine | Nval |
| D-N-methyltyrosine | Dnmtyr | N-methyla-napthylalanine | Nmanap |
| D-N-methylvaline | Dnmval | N-methylpenicillamine | Nmpen |
| γ-aminobutyric acid | Gabu | N-(p-hydroxyphenyl)glycine | Nhtyr |
| L-t-butylglycine | Tbug | N-(thiomethyl)glycine | Ncys |
| L-ethylglycine | Etg | penicillamine | Pen |
| L-homophenylalanine | Hphe | L-α-methylalanine | Mala |
| L-α-methylarginine | Marg | L-α-methylasparagine | Masn |
| L-α-methylaspartate | Masp | L-α-methyl-t-butylglycine | Mtbug |
| L-α-methylcysteine | Mcys | L-methylethylglycine | Metg |
| L-α-methylglutamine | Mgln | L-α-methylglutamate | Mglu |
| L-α ethylhistidine | Mhis | L-α-methylhomophenylalanine | Mhphe |
| L-α thylisoleucine | Mile | N-(2-methylthioethyl)glycine | Nmet |
| L-α-methylleucine | Mleu | L-α-methyllysine | Mlys |
| L-α-methylmethionine | Mmet | L-α-methylnorleucine | Mnle |
| L-α-methylnorvaline | Mnva | L-α-methylornithine | Morn |
| L-α-methylphenylalanine | Mphe | L-α-methylproline | Mpro |
| L-α-methylserine | mser | L-α-methylthreonine | Mthr |
| L-α ethylvaline | Mtrp | L-α-methyltyrosine | Mtyr |
| L-α-methylleucine | Mval<br>Nnbhm | L-N-methylhomophenylalanine | Nmhphe |
| N-(N-(2,2-diphenylethyl) carbamylmethyl-glycine | Nnbhm | N-(N-(3,3-diphenylpropyl) carbamylmethyl(1)glycine | Nnbhe |
| 1-carboxy-1-(2,2-diphenyl ethylamino)cyclopropane | Nmbc | | |

Table 2 Cont.

The present teachings further contemplate cyclic peptides or cyclic structures within the peptides. Methods of cyclization are well known in the art, see for instance in WO2010/041237, which is hereby incorporated by reference.

The cyclization may be via N- to C-terminal, N-terminal to side chain and N-terminal to backbone, C-terminal to side chain, C-terminal to backbone, side chain to backbone and side chain to side chain, as well as backbone to backbone cyclization.

Cyclization of the polypeptide may also take place through non-amino acid organic moieties comprised in the polypeptide.

For example, a peptide according to the teachings of the present invention can include at least two cysteine residues flanking the core peptide sequence (as described herein above). In this case, cyclization can be generated via formation of S—S bonds between the two Cys residues. Side chain to side chain cyclization can also be generated via formation of an interaction bond of the formula —(—$CH_2$-)n-S—$CH_2$—C—, wherein n=1 or 2, which is possible, for example, through incorporation of Cys or homoCys and reaction of its free SH group with, e.g., bromoacetylated Lys, Orn, Dab or Dap.

Furthermore, cyclization can be obtained, for example, through amide bond formation, e.g., by incorporating Glu, Asp, Lys, Orn, di-amino butyric (Dab) acid, di-aminopropionic (Dap) acid at various positions in the chain (—CO—NH or —NH—CO bonds). Backbone to backbone cyclization can also be obtained through incorporation of modified amino acids of the formulas H—N(($CH_2$)n-COOH)—C(R)H—COOH or H—N(($CH_2$)n-COOH)—C(R)H—$NH_2$, wherein n=1-4, and further wherein R is any natural or non-natural side chain of an amino acid.

Cyclic peptides can be joined together by a peptide bond, a disulfide linkage between two amino acid residues such as cysteine residues, or by any other suitable linking group. Nonpeptidal linking groups can be any chemical moiety that can react with functional groups at each end of the peptide chain to form a link therebetween. For example, two ends of a peptide chain can be linked together by a non-protein amino acid such as 3-aminobutyric acid or by a disulfide formed from nonpeptidal thiol groups such as a thioglycolic amide at the amino terminal end and amide formed from 2-aminoethane thiol at the carboxy terminal end, for example.

Hereinthroughout, the phrases "disulfide bridge" and "disulfide bond" are used interchangeably, and describe a —S—S— bond.

The linker may comprise additional amino acids linked together by peptide bonds which serve as spacers such that the linker does not interfere with the biological activity of the final compound. The linker is preferably made up of amino acids linked together by peptide bonds. Thus, in preferred embodiments, the linker is made up of from 1 to 10 amino acids linked by peptide bonds, wherein the amino acids are selected from the 20 naturally occurring amino acids. Some of these amino acids may be glycosylated, as is well understood by those in the art. In a more preferred embodiment, besides cysteine the amino acids in the linker are selected from glycine, alanine, proline, asparagine, glutamine, and lysine. Even more preferably, besides cysteine, the linker is made up of a majority of amino acids that are sterically unhindered, such as glycine and alanine.

Thus, according to one embodiment the linker comprises the sequence cysteine-glycine.

According to another embodiment the cyclization is effected using a coupling agent.

The term "coupling agent", as used herein, refers to a reagent that can catalyze or form a bond between two or more functional groups intra-molecularly, inter-molecularly or both. Coupling agents are widely used to increase polymeric networks and promote crosslinking between polymeric chains, hence, in the context of some embodiments of the present invention, the coupling agent is such that can promote crosslinking between polymeric chains; or such that can promote crosslinking between amino functional groups and carboxylic functional groups, or between other chemically compatible functional groups of polymeric chains. In some embodiments of the present invention the term "coupling agent" may be replaced with the term "crosslinking agent". In some embodiments, one of the polymers serves as the coupling agent and acts as a crosslinking polymer.

By "chemically compatible" it is meant that two or more types of functional groups can react with one another so as to form a bond.

According to some embodiments of the present invention, the coupling agent can be selected according to the type of functional groups and the nature of the crosslinking bond that can be formed therebetween. For example, carboxyl coupling directly to an amine can be afforded using a carbodiimide type coupling agent, such as EDC; amines may be coupled to carboxyls, carbonyls and other reactive functional groups by N-hydroxysuccinimide esters (NHS-esters), imidoester, PFP-ester or hydroxymethyl phosphine; sulfhydryls may be coupled to carboxyls, carbonyls, amines and other reactive functional groups by maleimide, haloacetyl (bromo- or iodo-), pyridyldisulfide and vinyl sulfone; aldehydes as in oxidized carbohydrates, may be coupled to other reactive functional groups with hydrazide; and hydroxyl may be coupled to carboxyls, carbonyls, amines and other reactive functional groups with isocyanate.

Hence, suitable coupling agents that can be used in some embodiments of the present invention include, but are not limited to, carbodiimides, NHS-esters, imidoesters, PFP-esters or hydroxymethyl phosphines.

It will be appreciated that additional peptides are contemplated by the present invention as well as those comprising the amino acid sequences disclosed herein, which may be synthesized (comprising conservative or non-conservative substitutions) in order to "tweak the system" and generate integrin αvβ3 binding peptides with improved characteristics i.e. comprising an enhanced ability to bind integrin αvβ3.

Thus, in other embodiments, the peptide comprises a homolog, a variant, or a functional fragment of the sequences described herein above. In another embodiment, the peptide monomers comprise an amino acid sequence that is about 95%, 96%, 97%, 98% or 99% identical to the sequences described herein above.

Typically, the amino acid substitution is a conservation substitution.

The term "conservative substitution" as used herein, refers to the replacement of an amino acid present in the native sequence in the peptide with a naturally or non-naturally occurring amino or a peptidomimetics having similar steric properties. Where the side-chain of the native amino acid to be replaced is either polar or hydrophobic, the conservative substitution should be with a naturally occurring amino acid, a non-naturally occurring amino acid or with a peptidomimetic moiety which is also polar or hydrophobic (in addition to having the same steric properties as the side-chain of the replaced amino acid).

As naturally occurring amino acids are typically grouped according to their properties, conservative substitutions by naturally occurring amino acids can be easily determined bearing in mind the fact that in accordance with the invention replacement of charged amino acids by sterically similar non-charged amino acids are considered as conservative substitutions.

For producing conservative substitutions by non-naturally occurring amino acids it is also possible to use amino acid analogs (synthetic amino acids) well known in the art. A peptidomimetic of the naturally occurring amino acid is well documented in the literature known to the skilled practitioner.

When affecting conservative substitutions the substituting amino acid should have the same or a similar functional group in the side chain as the original amino acid.

The phrase "non-conservative substitutions" as used herein refers to replacement of the amino acid as present in the parent sequence by another naturally or non-naturally occurring amino acid, having different electrochemical and/or steric properties. Thus, the side chain of the substituting amino acid can be significantly larger (or smaller) than the side chain of the native amino acid being substituted and/or can have functional groups with significantly different electronic properties than the amino acid being substituted. Examples of non-conservative substitutions of this type include the substitution of phenylalanine or cycohexylmethyl glycine for alanine, isoleucine for glycine, or $—NH—CH[(—CH_2)_5—COOH]—CO—$ for aspartic acid. Those non-conservative substitutions which fall under the scope of the present invention are those which still constitute a peptide having anti-bacterial properties.

The N and C termini of the peptides of the present invention may be protected by functional groups. Suitable functional groups are described in Green and Wuts, "Protecting Groups in Organic Synthesis", John Wiley and Sons, Chapters 5 and 7, 1991, the teachings of which are incorporated herein by reference.

Hydroxyl protecting groups include esters, carbonates and carbamate protecting groups. Amine protecting groups include alkoxy and aryloxy carbonyl groups, as described above for N-terminal protecting groups. Carboxylic acid protecting groups include aliphatic, benzylic and aryl esters, as described above for C-terminal protecting groups. In one embodiment, the carboxylic acid group in the side chain of one or more glutamic acid or aspartic acid residue in a peptide of the present invention is protected, preferably with a methyl, ethyl, benzyl or substituted benzyl ester.

Examples of N-terminal protecting groups include acyl groups (—CO—R1) and alkoxy carbonyl or aryloxy carbonyl groups (—CO—O—R1), wherein R1 is an aliphatic, substituted aliphatic, benzyl, substituted benzyl, aromatic or a substituted aromatic group. Specific examples of acyl groups include acetyl, (ethyl)-CO—, n-propyl-CO—, iso-propyl-CO—, n-butyl-CO—, sec-butyl-CO—, t-butyl-CO—, hexyl, lauroyl, palmitoyl, myristoyl, stearyl, oleoyl phenyl-CO—, substituted phenyl-CO—, benzyl-CO— and (substituted benzyl)-CO—. Examples of alkoxy carbonyl and aryloxy carbonyl groups include CH3-O—CO—, (ethyl)-O—CO—, n-propyl-O—CO—, iso-propyl-O—CO—, n-butyl-O—CO—, sec-butyl-O—CO—, t-butyl-O—CO—, phenyl-O—CO—, substituted phenyl-O—CO— and benzyl-O—CO—, (substituted benzyl)-O—CO—, adamantane, naphtalene, myristoleyl, toluene, biphenyl, cinnamoyl, nitrobenzoyl, toluoyl, furoyl, benzoyl, cyclohexane, norbornane, Z-caproic. In order to facilitate the N-acylation, one to four glycine residues can be present in the N-terminus of the molecule.

The carboxyl group at the C-terminus of the compound can be protected, for example, by an amide (i.e., the hydroxyl group at the C-terminus is replaced with $—NH_2$, $—NHR_2$ and $—NR_2R_3$) or ester (i.e. the hydroxyl group at the C-terminus is replaced with $—OR_2$). $R_2$ and $R_3$ are independently an aliphatic, substituted aliphatic, benzyl, substituted benzyl, aryl or a substituted aryl group. In addition, taken together with the nitrogen atom, R2 and $R_3$ can form a C4 to C8 heterocyclic ring with from about 0-2 additional heteroatoms such as nitrogen, oxygen or sulfur. Examples of suitable heterocyclic rings include piperidinyl, pyrrolidinyl, morpholino, thiomorpholino or piperazinyl. Examples of C-terminal protecting groups include $—NH_2$, $—NHCH_3$, $—N(CH_3)_2$, —NH(ethyl), $—N(ethyl)_2$, —N(methyl) (ethyl), —NH(benzyl), —N(C1-C4 alkyl) (benzyl), —NH(phenyl), —N(C1-C4 alkyl) (phenyl), $—OCH_3$, —O-(ethyl), —O-(n-propyl), —O-(n-butyl), —O-(iso-propyl), —O-(sec-butyl), —O-(t-butyl), —O— benzyl and —O-phenyl.

The peptides of the present invention may also comprise non-amino acid moieties, such as for example, hydrophobic moieties (various linear, branched, cyclic, polycyclic or heterocyclic hydrocarbons and hydrocarbon derivatives) attached to the peptides; various protecting groups, especially where the compound is linear, which are attached to the compound's terminals to decrease degradation. Chemical (non-amino acid) groups present in the compound may be included in order to improve various physiological properties such; decreased degradation or clearance; decreased repulsion by various cellular pumps, improve immunogenic activities, improve various modes of administration (such as attachment of various sequences which allow penetration through various barriers, through the gut, etc.); increased specificity, increased affinity, decreased toxicity and the like.

The peptides of the present invention can be biochemically synthesized such as by using standard solid phase techniques. These methods include exclusive solid phase synthesis, partial solid phase synthesis methods, fragment condensation, classical solution synthesis. Solid phase polypeptide synthesis procedures are well known in the art and further described by John Morrow Stewart and Janis Dillaha Young, Solid Phase Polypeptide Syntheses (2nd Ed., Pierce Chemical Company, 1984).

Synthetic peptides can be purified by preparative high performance liquid chromatography [Creighton T. (1983) Proteins, structures and molecular principles. WH Freeman and Co. N.Y.] and the composition of which can be confirmed via amino acid sequencing.

Recombinant techniques may also be used to generate the monomers of the present invention. To produce a peptide of the present invention using recombinant technology, a polynucleotide encoding the monomer of the present invention is ligated into a nucleic acid expression vector, which comprises the polynucleotide sequence under the transcriptional control of a cis-regulatory sequence (e.g., promoter sequence) suitable for directing constitutive, tissue specific or inducible transcription of the monomers of the present invention in the host cells.

In addition to being synthesizable in host cells, the peptides of the present invention can also be synthesized using in vitro expression systems. These methods are well known in the art and the components of the system are commercially available.

The peptides of the present invention may also comprise non-amino acid moieties, such as for example, hydrophobic moieties (various linear, branched, cyclic, polycyclic or heterocyclic hydrocarbons and hydrocarbon derivatives) attached to the peptides; various protecting groups, especially where the compound is linear, which are attached to the compound's terminals to decrease degradation. Chemical (non-amino acid) groups present in the compound may be included in order to improve various physiological properties such; decreased degradation or clearance; decreased repulsion by various cellular pumps, improve immunogenic activities, improve various modes of administration (such as attachment of various sequences which allow penetration through various barriers, through the gut, etc.); increased specificity, increased affinity, decreased toxicity and the like.

According to one embodiment, the peptides of the present invention are attached to a sustained-release enhancing agent. Exemplary sustained-release enhancing agents include, but are not limited to hyaluronic acid (HA), alginic acid (AA), polyhydroxyethyl methacrylate (Poly-HEMA), polyethylene glycol (PEG), glyme and polyisopropylacrylamide.

Attaching the amino acid sequence component of the peptides of the invention to other non-amino acid agents may be by covalent linking, by non-covalent complexion, for example, by complexion to a hydrophobic polymer, which can be degraded or cleaved producing a compound capable of sustained release; by entrapping the amino acid part of the peptide in liposomes or micelles to produce the final peptide of the invention. The association may be by the entrapment of the amino acid sequence within the other component (liposome, micelle) or the impregnation of the amino acid sequence within a polymer to produce the final peptide of the invention.

It will be appreciated that for therapeutic purposes, the peptides of the present invention may be attached to a therapeutic moiety.

The therapeutic moiety can be, for example, a cytotoxic moiety, a toxic moiety, a cytokine moiety and a second antibody moiety comprising a different specificity to the antibodies of the invention.

Non-limiting examples of therapeutic moieties which can be conjugated to the peptide of the invention are provided in Table 3, hereinbelow.

TABLE 3

| Therapeutic moiety | Amino acid sequence (GenBank Accession No.) | Nucleic acid sequence (GenBank Accession No.) |
|---|---|---|
| *Pseudomonas* exotoxin | ABU63124 | EU090068 |
| Diphtheria toxin | AAV70486 | AY820132.1 |
| interleukin 2 | CAA00227 | A02159 |
| CD3 | P07766 | X03884 |
| CD16 | NP_000560.5 | NM_000569.6 |
| interleukin 4 | NP_000580.1 | NM_000589.2 |
| HLA-A2 | P01892 | K02883 |
| interleukin 10 | P22301 | M57627 |
| Ricin toxin | EEF27734 | EQ975183 |

It will be appreciated that the peptides of this aspect of the present invention may also be attached to detectable moieties. These peptides can then be used to detect cells which express αvβ3 on their surface. The detection may be effected in vivo or in vitro. The detectable moiety can be a label which is directly visualized (e.g., a fluorescent molecule, a radioactive molecule) or a member of a binding (affinity) pair, which is identifiable via its interaction with an additional member of the binding pair (e.g., antibody-antigen pairs, enzyme-substrate pairs). Table 4, hereinbelow, provides examples of sequences of identifiable moieties.

TABLE 4

| Identifiable Moiety | Amino Acid sequence (Genebank Accession No.) | Nucleic Acid sequence (Genebank Accession No.) |
|---|---|---|
| Green Fluorescent protein | AAL33912 | AF435427 |
| Alkaline phosphatase | AAK73766 | AY042185 |
| Peroxidase | NP_568674 | NM_124071 |
| Histidine tag | AAK09208 | AF329457 |
| Myc tag | AF329457 | AF329457 |
| Biotin lygase tag | NP_561589 | NC_003366 |
| orange fluorescent protein | AAL33917 | AF435432 |
| Beta galactosidase | NM_125776 | NM_125776 |
| Fluorescein isothiocyanate | AAF22695 | AF098239 |
| Streptavidin | S11540 | S11540 |

The functional moiety (the detectable or therapeutic moiety) may be attached or conjugated to the peptides of the invention in various ways, depending on the context, application and purpose.

When the functional moiety is a polypeptide, the conjugate may be produced by recombinant means. For example, the nucleic acid sequence encoding a toxin (e.g., PE38KDEL) or a fluorescent protein [e.g., green fluorescent protein (GFP), red fluorescent protein (RFP) or yellow fluorescent protein (YFP)] may be ligated in-frame with the nucleic acid sequence encoding the peptide of the invention and be expressed in a host cell to produce a recombinant conjugated peptide. Alternatively, the functional moiety may be chemically synthesized by, for example, the stepwise addition of one or more amino acid residues in defined order such as solid phase peptide synthetic techniques.

A functional moiety may also be attached to the antibody of the invention using standard chemical synthesis techniques widely practiced in the art [see e.g., hypertexttransferprotocol://worldwideweb (dot) chemistry (dot) org/portal/Chemistry)], such as using any suitable chemical linkage, direct or indirect, as via a peptide bond (when the functional moiety is a polypeptide), or via covalent bonding to an intervening linker element, such as a linker peptide or other chemical moiety, such as an organic polymer. Chimeric peptides may be linked via bonding at the carboxy (C) or amino (N) termini of the peptides, or via bonding to internal chemical groups such as straight, branched or cyclic side chains, internal carbon or nitrogen atoms, and the like. Description of fluorescent labeling of proteins is provided in details in U.S. Pat. Nos. 3,940,475, 4,289,747, and 4,376,110.

Exemplary methods for conjugating peptide moieties (therapeutic or detectable moieties) to the peptide of the invention are described herein below:

SPDP Conjugation—

A non-limiting example of a method of SPDP conjugation is described in Cumber et al. (1985, Methods of Enzymology 112: 207-224). Briefly, a peptide, such as a detectable or therapeutic moiety (e.g., 1.7 mg/ml) is mixed with a 10-fold excess of SPDP (50 mM in ethanol); the antibody is mixed with a 25-fold excess of SPDP in 20 mM sodium phosphate, 0.10 M NaCl pH 7.2 and each of the reactions is incubated for about 3 hours at room temperature. The reactions are then dialyzed against PBS. The peptide is reduced, e.g., with 50 mM DTT for 1 hour at room temperature. The reduced peptide is desalted by equilibration on G-25 column (up to 5% sample/column volume) with 50 mM $KH_2PO_4$ pH 6.5. The reduced peptide is combined with the SPDP-antibody in a molar ratio of 1:10 antibody:peptide and incubated at 4° C. overnight to form a peptide-antibody conjugate.

Glutaraldehyde Conjugation—

A non-limiting example of a method of glutaraldehyde conjugation is described in G. T. Hermanson (1996, "Antibody Modification and Conjugation, in Bioconjugate Techniques, Academic Press, San Diego). Briefly, the antibody and the peptide (1.1 mg/ml) are mixed at a 10-fold excess with 0.05% glutaraldehyde in 0.1 M phosphate, 0.15 M NaCl pH 6.8, and allowed to react for 2 hours at room temperature. 0.01 M lysine can be added to block excess sites. After-the reaction, the excess glutaraldehyde is removed using a G-25 column equilibrated with PBS (10% v/v sample/column volumes).

Carbodiimide Conjugation—

Conjugation of a peptide with an antibody can be accomplished using a dehydrating agent such as a carbodiimide, e.g., in the presence of 4-dimethyl aminopyridine. Carbodiimide conjugation can be used to form a covalent bond between a carboxyl group of peptide and an hydroxyl group of an antibody (resulting in the formation of an ester bond), or an amino group of an antibody (resulting in the formation of an amide bond) or a sulfhydryl group of an antibody (resulting in the formation of a thioester bond). Likewise, carbodiimide coupling can be used to form analogous covalent bonds between a carbon group of an antibody and an hydroxyl, amino or sulfhydryl group of the peptide [see, J. March, Advanced Organic Chemistry: Reaction's, Mechanism, and Structure, pp. 349-50 & 372-74 (3d ed.), 1985]. For example, the peptide can be conjugated to an antibody via a covalent bond using a carbodiimide, such as dicyclohexylcarbodiimide [B. Neises et al. (1978), Angew Chem., Int. Ed. Engl. 17:522; A. Hassner et al. (1978, Tetrahedron Lett. 4475); E. P. Boden et al. (1986, J. Org. Chem. 50:2394) and L. J. Mathias (1979, Synthesis 561)].

The peptides of some embodiments of the invention can be administered to an organism per se, or in a pharmaceutical composition where it is mixed with suitable carriers or excipients.

As used herein a "pharmaceutical composition" refers to a preparation of one or more of the active ingredients described herein with other chemical components such as physiologically suitable carriers and excipients. The purpose of a pharmaceutical composition is to facilitate administration of a compound to an organism.

Herein the term "active ingredient" refers to the peptide accountable for the biological effect.

Hereinafter, the phrases "physiologically acceptable carrier" and "pharmaceutically acceptable carrier" which may be interchangeably used refer to a carrier or a diluent that does not cause significant irritation to an organism and does not abrogate the biological activity and properties of the administered compound. An adjuvant is included under these phrases.

Herein the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences," Mack Publishing Co., Easton, Pa., latest edition, which is incorporated herein by reference.

Suitable routes of administration may, for example, include oral, rectal, transmucosal, especially transnasal, intestinal or parenteral delivery, including intramuscular, subcutaneous and intramedullary injections as well as intrathecal, direct intraventricular, intracardiac, e.g., into the right or left ventricular cavity, into the common coronary artery, intravenous, intraperitoneal, intranasal, or intraocular injections.

Conventional approaches for drug delivery to the central nervous system (CNS) include: neurosurgical strategies (e.g., intracerebral injection or intracerebroventricular infusion); molecular manipulation of the agent (e.g., production of a chimeric fusion protein that comprises a transport peptide that has an affinity for an endothelial cell surface molecule in combination with an agent that is itself incapable of crossing the BBB) in an attempt to exploit one of the endogenous transport pathways of the BBB; pharmacological strategies designed to increase the lipid solubility of an agent (e.g., conjugation of water-soluble agents to lipid or cholesterol carriers); and the transitory disruption of the integrity of the BBB by hyperosmotic disruption (resulting from the infusion of a mannitol solution into the carotid artery or the use of a biologically active agent such as an angiotensin peptide).

However, each of these strategies has limitations, such as the inherent risks associated with an invasive surgical procedure, a size limitation imposed by a limitation inherent in the endogenous transport systems, potentially undesirable biological side effects associated with the systemic administration of a chimeric molecule comprised of a carrier motif that could be active outside of the CNS, and the possible risk of brain damage within regions of the brain where the BBB is disrupted, which renders it a suboptimal delivery method.

Alternately, one may administer the pharmaceutical composition in a local rather than systemic manner, for example, via injection of the pharmaceutical composition directly into a tissue region of a patient.

The term "tissue" refers to part of an organism consisting of cells designed to perform a function or functions. Examples include, but are not limited to, brain tissue, retina, skin tissue, hepatic tissue, pancreatic tissue, bone, cartilage, connective tissue, blood tissue, muscle tissue, cardiac tissue brain tissue, vascular tissue, renal tissue, pulmonary tissue, gonadal tissue, hematopoietic tissue.

Pharmaceutical compositions of some embodiments of the invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with some embodiments of the invention thus may be formulated in conventional manner using one or more physiologically acceptable carriers comprising excipients and auxiliaries, which facilitate processing of the active ingredients into preparations which, can be used pharmaceutically. Proper formulation is dependent upon the route of administration chosen.

For injection, the active ingredients of the pharmaceutical composition may be formulated in aqueous solutions, preferably in physiologically compatible buffers such as Hank's solution, Ringer's solution, or physiological salt buffer. For transmucosal administration, penetrants appropriate to the barrier to be permeated are used in the formulation. Such penetrants are generally known in the art.

For oral administration, the pharmaceutical composition can be formulated readily by combining the active compounds with pharmaceutically acceptable carriers well known in the art. Such carriers enable the pharmaceutical composition to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carbomethylcellulose; and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active compound doses.

Pharmaceutical compositions which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active ingredients may be dissolved or suspended in suitable liquids, such as fatty oils, liquid paraffin, or liquid polyethylene glycols. In addition, stabilizers may be added.

All formulations for oral administration should be in dosages suitable for the chosen route of administration.

For buccal administration, the compositions may take the form of tablets or lozenges formulated in conventional manner.

For administration by nasal inhalation, the active ingredients for use according to some embodiments of the invention are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in a dispenser may be formulated containing a powder mix of the compound and a suitable powder base such as lactose or starch.

The pharmaceutical composition described herein may be formulated for parenteral administration, e.g., by bolus injection or continuous infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the active preparation in water-soluble form. Additionally, suspensions of the active ingredients may be prepared as appropriate oily or water based injection suspensions. Suitable lipophilic solvents or vehicles include fatty oils such as sesame oil, or synthetic fatty acids esters such as ethyl oleate, triglycerides or liposomes.

Aqueous injection suspensions may contain substances, which increase the viscosity of the suspension, such as sodium carboxymethyl cellulose, sorbitol or dextran. Optionally, the suspension may also contain suitable stabilizers or agents which increase the solubility of the active ingredients to allow for the preparation of highly concentrated solutions.

Alternatively, the active ingredient may be in powder form for constitution with a suitable vehicle, e.g., sterile, pyrogen-free water based solution, before use.

The pharmaceutical composition of some embodiments of the invention may also be formulated in rectal compositions such as suppositories or retention enemas, using, e.g., conventional suppository bases such as cocoa butter or other glycerides.

Pharmaceutical compositions suitable for use in context of some embodiments of the invention include compositions wherein the active ingredients are contained in an amount effective to achieve the intended purpose. More specifically, a therapeutically effective amount means an amount of active ingredients (peptide) effective to prevent, alleviate or ameliorate symptoms of a disorder (e.g., cancer) or prolong the survival of the subject being treated.

Determination of a therapeutically effective amount is well within the capability of those skilled in the art, especially in light of the detailed disclosure provided herein.

For any preparation used in the methods of the invention, the therapeutically effective amount or dose can be estimated initially from in vitro and cell culture assays. For example, a dose can be formulated in animal models to achieve a desired concentration or titer. Such information can be used to more accurately determine useful doses in humans.

Toxicity and therapeutic efficacy of the active ingredients described herein can be determined by standard pharmaceutical procedures in vitro, in cell cultures or experimental animals. The data obtained from these in vitro and cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition. (See e.g., Fingl, et al., 1975, in "The Pharmacological Basis of Therapeutics", Ch. 1 p. 1).

Dosage amount and interval may be adjusted individually to ensure that levels of the active ingredient are sufficient to induce or suppress the biological effect (minimal effective concentration, MEC). The MEC will vary for each preparation, but can be estimated from in vitro data. Dosages necessary to achieve the MEC will depend on individual characteristics and route of administration. Detection assays can be used to determine plasma concentrations.

Depending on the severity and responsiveness of the condition to be treated, dosing can be of a single or a plurality of administrations, with course of treatment lasting from several days to several weeks or until cure is effected or diminution of the disease state is achieved.

The amount of a composition to be administered will, of course, be dependent on the subject being treated, the severity of the affliction, the manner of administration, the judgment of the prescribing physician, etc.

Compositions of some embodiments of the invention may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert. Compositions comprising a preparation of the invention formulated in a compatible pharmaceutical carrier may also be prepared, placed in an appropriate container, and labeled for treatment of an indicated condition, as is further detailed above.

The term "treating" refers to inhibiting, preventing or arresting the development of a pathology (disease, disorder or condition) and/or causing the reduction, remission, or regression of a pathology. Those of skill in the art will understand that various methodologies and assays can be used to assess the development of a pathology, and similarly, various methodologies and assays may be used to assess the reduction, remission or regression of a pathology.

As used herein, the term "preventing" refers to keeping a disease, disorder or condition from occurring in a subject who may be at risk for the disease, but has not yet been diagnosed as having the disease.

As used herein, the term "subject" includes mammals, preferably human beings at any age which suffer from the pathology. Preferably, this term encompasses individuals who are at risk to develop the pathology.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N.Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Materials and Methods

In Vitro Assays

Cell lines: All cells were cultured in RPMI1640 supplemented with 10% heat-inactivated FBS and antibiotics.

Reagents and chemicals: Primary antibodies against ERK1/2 and phosphoERK1/2 were from Santa Cruz Biotechnology. β-Tubulin (Cell signaling technology) was used to normalize the proteins loaded onto the membrane.

Viability: WST-1 (Roche; 10% final concentration) was incubated with cells at 37° C. for 2 h and read with a microELISA reader at 440 nm.

Flow cytometry: For Annexin-propidium iodide (PI) assay, cells were harvested and incubated with Annexin v-FITC and PI (BioVision) according to manufacturer's instructions and analyzed by flow cytometry. $Annexin^-/PI^-$, surviving cell fraction; $Annexin^+/PI^-$, early apoptosis; and $Annexin^+/PI^-$, late apoptosis.

Western blotting: Whole cell lysates were separated on 10-12.5% polyacrylamide gels, fast-transferred to PVDF membranes, incubated with the indicated antibodies and visualized using horseradish peroxidase (HRP)-conjugated secondary antibody (1:10,000, Jackson Immuno Research Laboratories) followed by enhanced chemiluminescence (ECL) detection (Biological Industries). Integrated optical densities of the bands were measured by Image reader Las3000, Multi-gauge v3.0 software.

BrdU incorporation: BrdU (Exalpha Biologicals, Inc. Shirley, Mass., USA) was added overnight to treated cells, after which the cells were fixed, permeabilized and the DNA denatured. An anti-BrdU monoclonal antibody was added for one hour, followed by addition of horseradish peroxidase-conjugated goat anti-mouse antibody.

The color reaction of the tetra-methylbenzidine (TMB) product was quantified using a spectrophotometer.

Phage Display

The purpose of this study was to identify peptides with binding affinity to the Integrin αvβ3. To achieve this aim a phage display platform was employed that allow screening of library of 109 peptides that displayed on the phage surface. Specifically in this method randomized sequences were expressed on the phage surface and 7-amino acid peptides with highest affinity for the Integrin αvβ3 were selected through repeated rounds of biopanning.

A M13 phage peptide surface display library (New England Biolabs, Ph.D.™-C7C Disulfide Constrained Peptide Library Kit, E8121L) was used for screening. The library contained phages displaying random disulfide-constrained heptapeptide sequences expressed at the amino-terminus of the M13 pIII minor coat protein.

Five microliter (7.5×1010 pfu) of the phage library were incubated with Integrin αvβ3 coated on concentration of 5 ug/well on microtiter wells. After four washes with phosphate-buffered saline, bound phages were eluted to enrich cyclic peptides and subjected to titration and amplification in the bacterial host strain *E. coli*. After fourth round of biopanning bound phages were recovered and randomly selected for further sequencing and bioinformatics analysis. The entire procedure was repeated twice and peptides with highest frequency that were overlapped in two sessions were sent for synthesis.

The peptide sequences flanked by the two cysteine residues of the M13 minor coat protein pIII are summarized in Table 5, herein below.

TABLE 5

| Peptide ID | SEQ ID NO | Amino acids (ABR) | Nucleic acids (with Cys seq) | SEQ ID NO: |
|---|---|---|---|---|
| ALOS-1 | 1 | CNLSSSWIC | TGT AAT CTT TCG TCT TCA TGG ATT TGC | 6 |
| ALOS-2 | 2 | CPPSNHLLC | TGT CCG CCG TCT AAT CAT CTG TTG TGC | 7 |
| ALOS-3 | 3 | CAPSPSRLC | TGT GCT CCT TCT CCT TCT CGG CTT TGC | 8 |
| ALOS-4 | 4 | CSSAGSLFC | TGT TCT TCT GCT GGT TCT CTT TTT TGC | 9 |
| ALOS-5 | 5 | CPLHARLPC | TGT CCG CTT CAT GCG CGG CTG CCT TGC | 10 |

Peptide preparation: Upon synthesis, peptides were purified by reverse-phase HPLC and their structures were confirmed by mass spectroscopy. Before use, peptides were dissolved in 0.01% BSA in saline, aliquoted and stored at −80° C. until use. For binding experiments peptides were labeled with fluorescein (FITC).

Integrin coated plates: 96 well plates (Greiner Cat no. 655075) were incubated overnight at 4° C. with 200 μl/well of coating buffer (TBS-Tween 0.05%, pH 7.6) containing 0.3 ug Integrin αvβ3. Wells were subsequently washed twice with TBS buffer.

Binding assay: The binding of peptides to immobilized purified integrin alpha-v-beta3 was evaluated using a fluorescein (FITC) labeled peptides. Purified integrin alpha-v-beta3 was first immobilized onto high-protein binding 96-well plates for 2 hour at 37° C. followed by blocking for two hours with κ% fat dry milk in TBS. After that, plates were washed four times with 200 μl TBS. a) For saturation assays plates were incubated with 100 μl of FITC-labeled peptides solutions in 0.01% BSA in Saline for 30 min at RT. B) For competition assays plates were incubated with different concentrations of unlabeled peptides for 30 min in RT followed by addition of fixed concentration of FITC-labeled peptides and additional incubation for 30 min. Wells were washed twice with TBS. After second wash 100 μl of TBS was added to the each well and fluorescence signal was read at excitation 490 nm and emission 525 nm using Enspire Plate reader (PerkinElmer). Binding data analysis was performed using Prism software (GraphPad Software, San Diego, Calif.). Binding curves were fit using nonlinear regression approaches.

In Vivo Studies

Metastatic Melanoma Mice Model Using B16F10 Cells.

Murine B16F10 cells grown in RPMI were harvested by trypsinization and washed with PBS. The cells were counted and resuspended in PBS to final concentrations of $1.0\times10^5$ cells/mL and were maintained at 4° C. for immediate i.v inoculation into the tail vein of C57BL6 male mice (Harlan Labs). Next day, following tumor cell inoculation, these animals received i.p. injection of ALOS peptide or saline. Injections were performed daily throughout the working week. Mice were weighed daily on the day of injection.

The cell viability was determined by trypan blue dye and exceeded 95%.

For analysis of the peptides' effect on melanoma nodule formation all mice were sacrificed 18 days following the i.v. injection. Organs were dissected analyzed visually. The lungs of sacrificed mice were rinsed in saline and fixed with Bouin's solution. The total number of visible nodules on the lung surface per animal was counted.

For analysis of the peptides' effect on survival of melanoma cell-inoculated mice, animals were observed several times a week for signs of lethargy such as weight loss, hunched position and epilepsy. In order to lessen suffering, when these symptoms occurred, mice were euthanized with cervical dislocation after $CO_2$ anesthesia. Survival time was recorded and long-term survivors were defined as animals surviving longer than 3 times the median survival of non-treated animals.

Example 1

In Vitro Cell Experiments

The different peptides were examined (100 nM-50 μM) in ovarian cancer (OVCAR3), cervical cancer (HeLa), mouse melanoma (B16) and breast cancer (MCF7) cells. HEK293 were used as negative normal control. The peptides were assessed for: cell death (Annexin-PI, FACS), proliferation (Brdu, ELISA), MAPK activation (Western) and viability (WST-1, ELISA).

ALOSs Affected Proliferation and Survival of Ovarian and Cervical Cancer

Figures 1A, 1B, 1C:
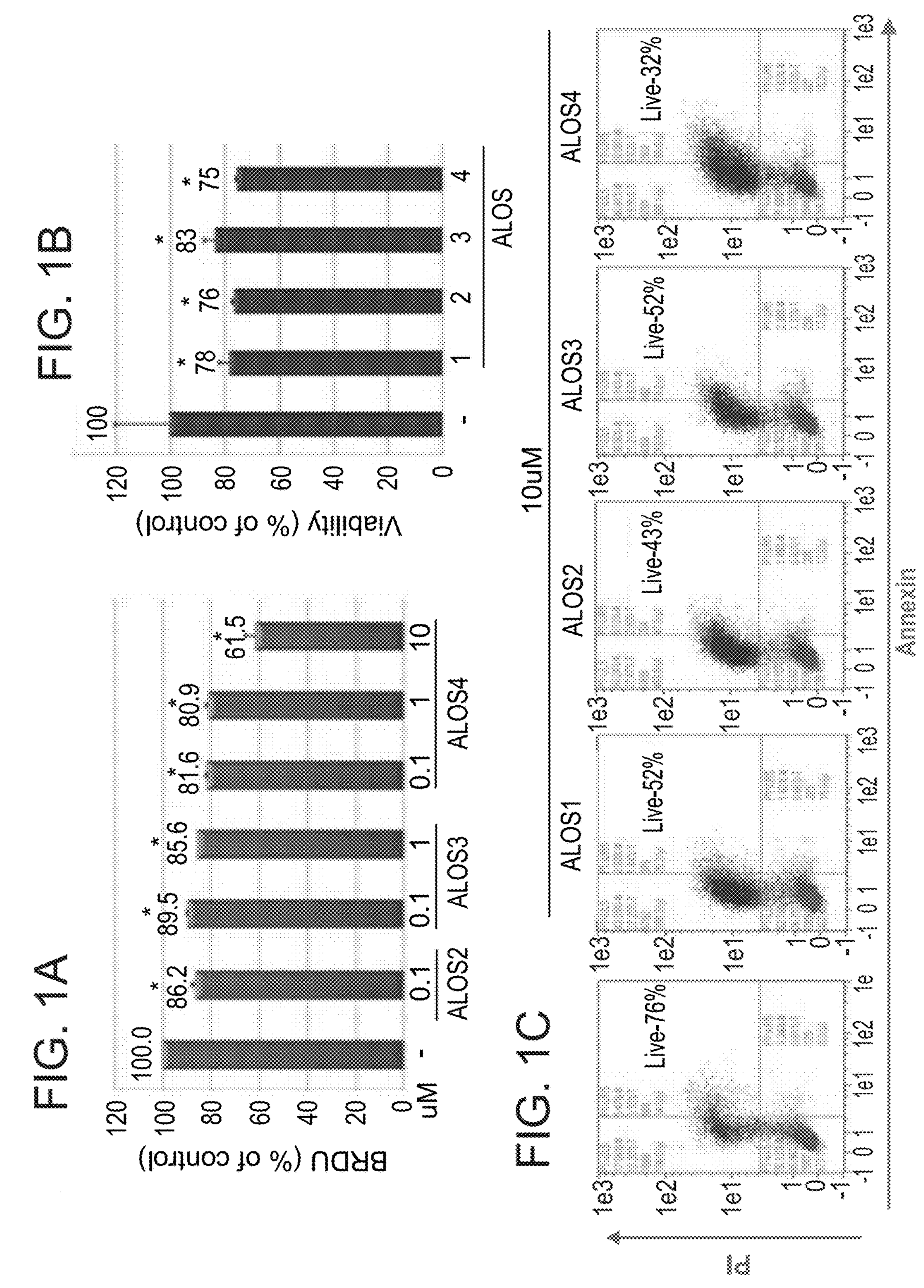
FIGS. 1A-1C illustrate proliferation and survival assays in cancer cells. OVCAR-3 cells were treated with the different peptides for 4-7 days and examined for cell proliferation (A). Cervical cancer cells (HeLa Cells) were treated with the different peptides for 4-7 days and examined for cell viability (B) and apoptosis (C) by annexin-PI assay.
Figure 7:
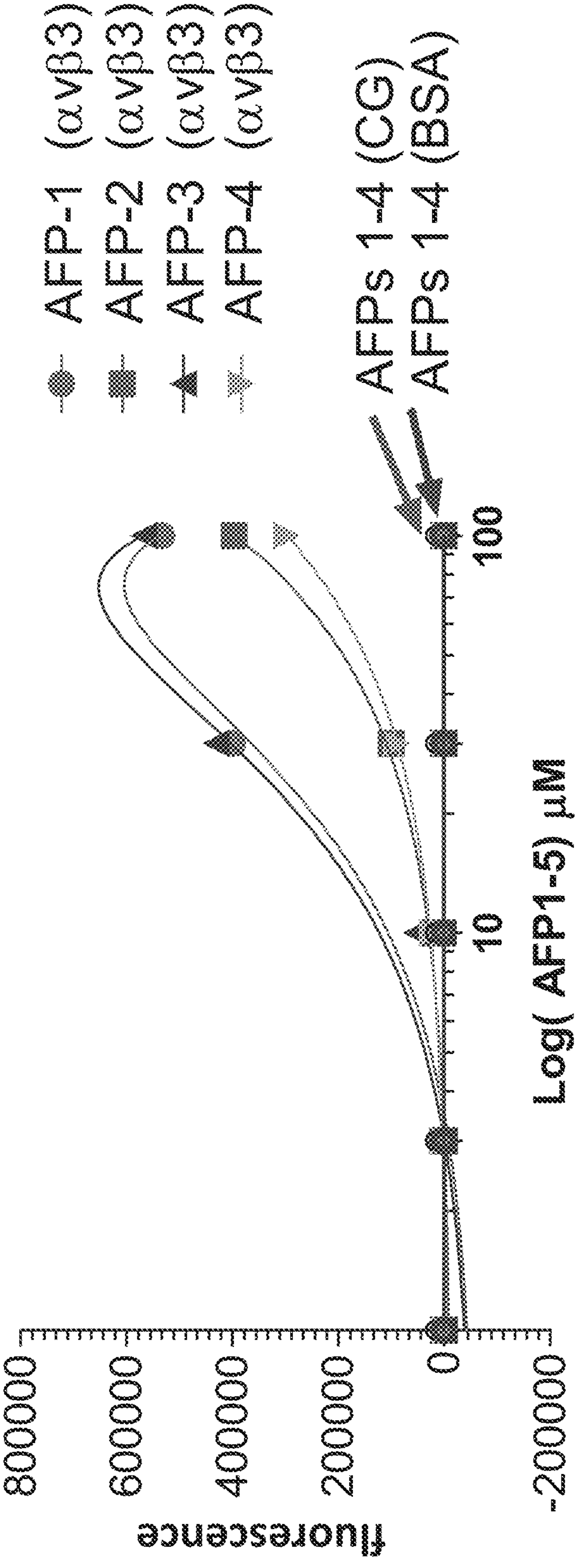
FIG. 7 is a graph illustrating binding of Fluorescein (FITC)—labeled ALOS peptides to purified Integrin $\alpha v\beta 3$, collagen (CG) and bovine serum albumin (BSA). Peptides (concentrations 100 uM, 30 uM, 10 uM, luM) were added to integrin pre-coated wells for 30 min. The fluorescence was measured using Enspire plate reader (PerkinElmer). The plots were built using nonlinear regression analysis (GraphPad Prism).

The various ALOS peptides differentially reduced ovarian (FIG. 1A, 96 h) cell proliferation (BRDU) and cervical cancer cell viability (FIG. 1B, 7 days) and increase apoptotic cell death (FIG. 1C, 7 days).

Figure 2A:
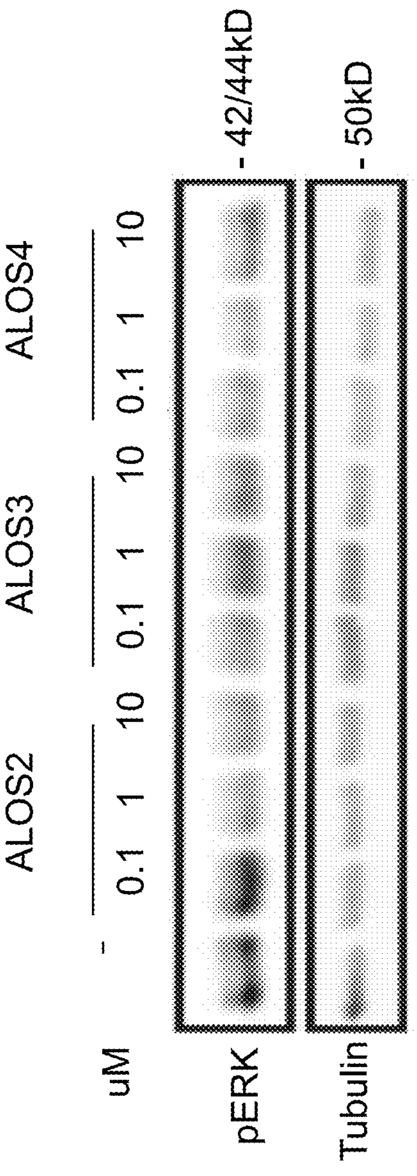
FIGS. 2A-2C illustrate pERK inhibition by the ALOS peptides. Western blots analyses for pERK were performed on whole cell lysates of (A) ovarian cancer OVCAR-3 cells, (B) cervical cancer cells, HeLa and (C) control normal cells (HEK-293) following treatment with the different peptides over a dose range. Total ERK1/2 protein was used for normalization.
Figure 2B:
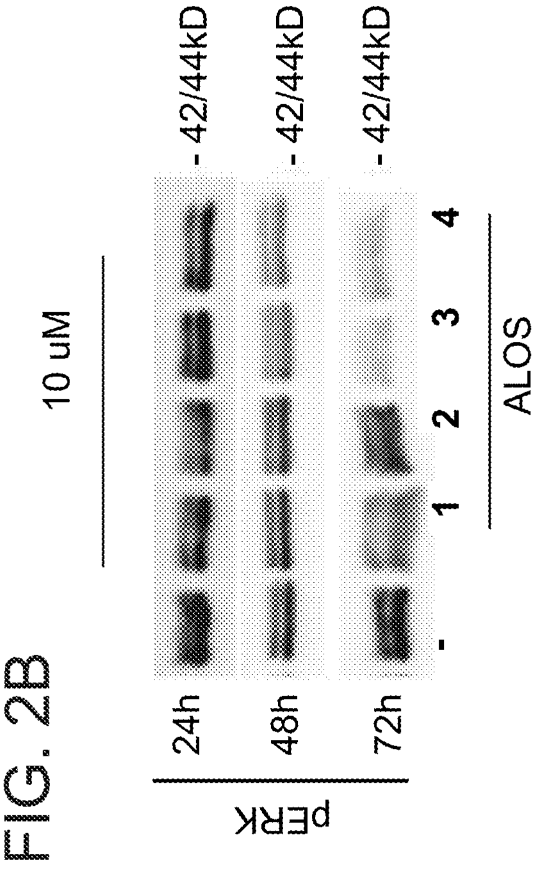
Figure 2C:
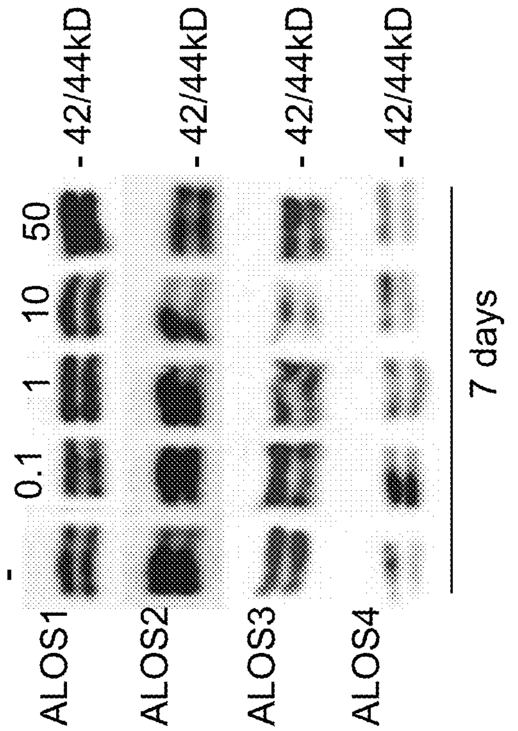

ALOS 2-4 Reduced pERK Activation in Ovarian and Cervical Cancer pERK activation, a central mitogenic pathway in cancer was examined by Western blot analysis (FIGS. 2A-C). ALOS2-4 reduced pERK in a dose dependent manner in (FIG. 2A) ovarian cancer (24 h) and a time dependent effect (24-72 h) in (FIG. 2B) cervical cancer. No effect after 7 days in normal control cells was observed (FIG. 2C, HEK293).

Example 2

In Vivo Experiments

ALOS3 and ALOS4 Block Melanoma Growth in Metastatic Melanoma Mice Model:

An important clinical problem of malignant tumors is that lethality is mostly attributed to metastasis of the primary neoplastic cells. Complete eradication of the primary malignant cells is usually limited, due to location of the tumor, spread to distant organs and severe side effects caused by treatment. The effects of ALOS 3 and 4 on artificial metastasis, using highly metastatic melanoma B16-F10 cells was studied. $5\times10^4$ cells of B16-F10/0.2 ml/mouse were injected into the tail vein of 8 weeks old C57BL/6 mice. 0.3 mg/kg of ALOS3 or ALOS4 was administered daily intraperitoneally following engrafting. 18 days later the mice were sacrificed, lungs were dissected and the total number of visible nodules on the lung surface was counted. As demonstrated in FIG. 3, daily 0.3 mg/kg administration of ALOS3 and more potently ALOS4 significantly blocked the number of metastatic melanoma sites in the lungs.

ALOS3 and ALOS4 Prevented Animals' Weight Reduction in Metastatic Melanoma Mice Model:

Animals' weight was tested during treatment course. As demonstrated in FIG. 4, saline treated animals exhibited gradual weight reduction during the experiments, while ALOS3 and ALOS4 treated animals did not show weight loss, rather they exhibited a constant weight gain during the experiment.

ALOS3 and ALOS4 Significantly Increased Survival of Metastatic Melanoma Mice Model:

The effect of ALOS3 and ALOS4 on artificial metastasis using highly metastatic melanoma B16-F10 cells was studied. $5\times10^3$ cells of B16-F10/0.2 ml/mouse were injected into the tail vein of 8 weeks old C57BL/6 mice. 0.3 mg/kg of ALOS3 or ALOS4 was administered daily intraperitoneally, following engrafting. Animals' survival was documented. As demonstrated in FIG. 5, daily 0.3 mg/kg administration of ALOS3 and more potently ALOS4 significantly increased the survival in comparison to saline treated controls.

ALOS3 and ALOS4 Showed Pronounced Anxiolytic Effect in Metastatic Melanoma Mice Model:

The EPM test was used to assess anxiety-like behavior of mice treated with chronic (0.3 mg/kg) doses of ALOS3 or ALOS4. The EPM apparatus comprises two closed (10 cm×45 cm×40 cm) and two open (10 cm×45 cm) arms that extend from a common central platform (10 cm×10 cm). The black apparatus is elevated to a height of 60 cm above floor level. The tests were conducted at the same time of the day (10.00-12.00 h) during the period of illumination in the mice's colony room. For habituation, all animals were placed in the experimental room one hour prior to the test. Each animal was placed at the center of the maze, facing one of the closed arms. Each mouse spent a five minute session in the EPM, during which the number of entries into open and closed arms as well as time spent in the open and closed arms were video scored. Results indicate that both ALOS3 and ALOS4 significantly increased the performance of the mice, indicating a beneficial effect on anxiety in comparison to the performance of the control group.

Example 3

Binding Experiments

ALOSs Bind Selectively to αvβ3 Integrin, but not to Collagen or BSA

In saturation experiments, total binding is determined at increasing concentrations of labeled ligand. As demonstrated in FIG. 7, fluorescence density of ALOS peptides was strongly and positively correlated with concentration of FITs-labeled peptides when tested on wells coated with αvβ3. In contrast, peptides failed to bind to wells coated with collagen or BSA. This study demonstrates ALOSs' specific binding affinity to αvβ3.

Scramble Peptides do not Bind to the αvβ3 Integrin

Figure 8:
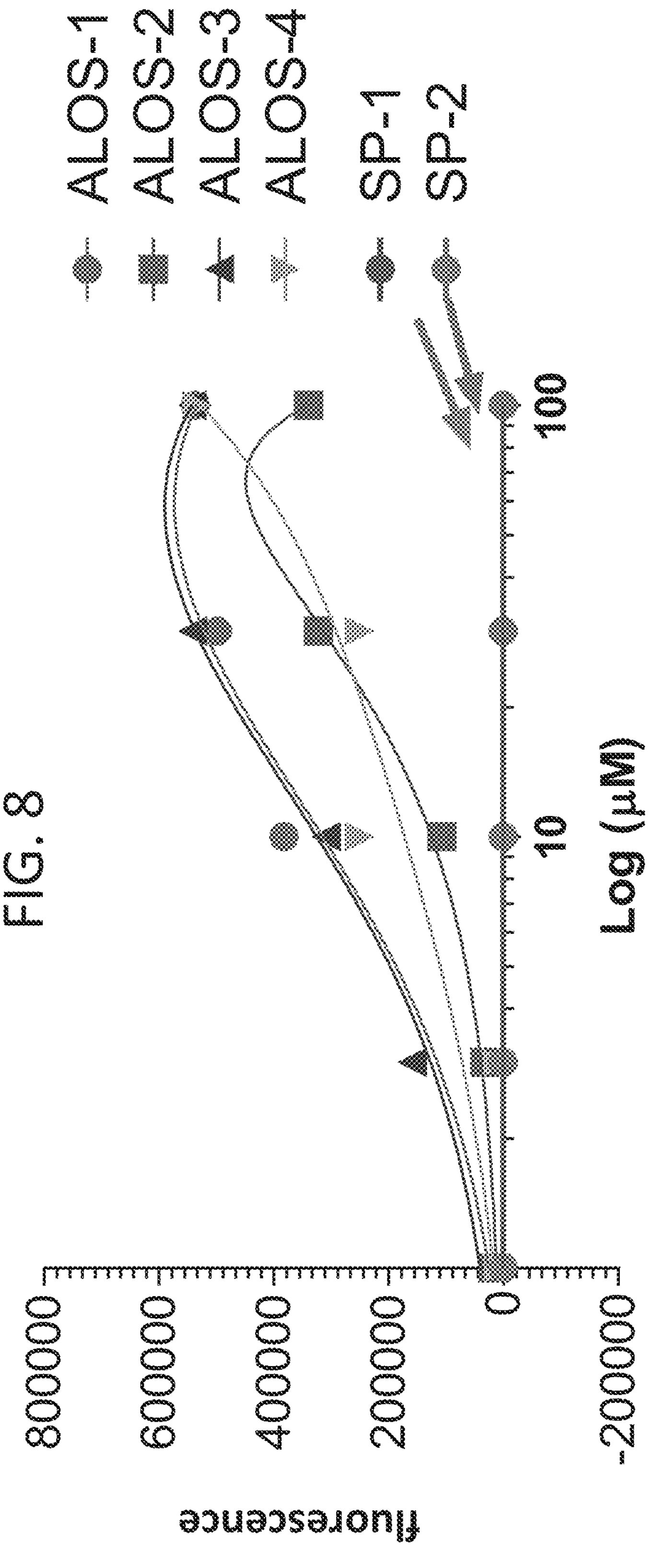
FIG. 8 is a graph illustrating the binding affinity of ALOS peptides to the Integrin $\alpha v\beta 3$ in comparison to scrambled FITC-labeled 7 amino acids peptides (SP1 and SP2). Peptides were added to integrin for 30 min. SP-1-scrambled peptide 1. SP-2-scrambled peptide 2. The fluorescence was measured using Enspire plate reader (PerkinElmer). The plots were built using nonlinear regression analysis (GraphPad Prism).
Figures 9A, 9B, 9C, 9D:
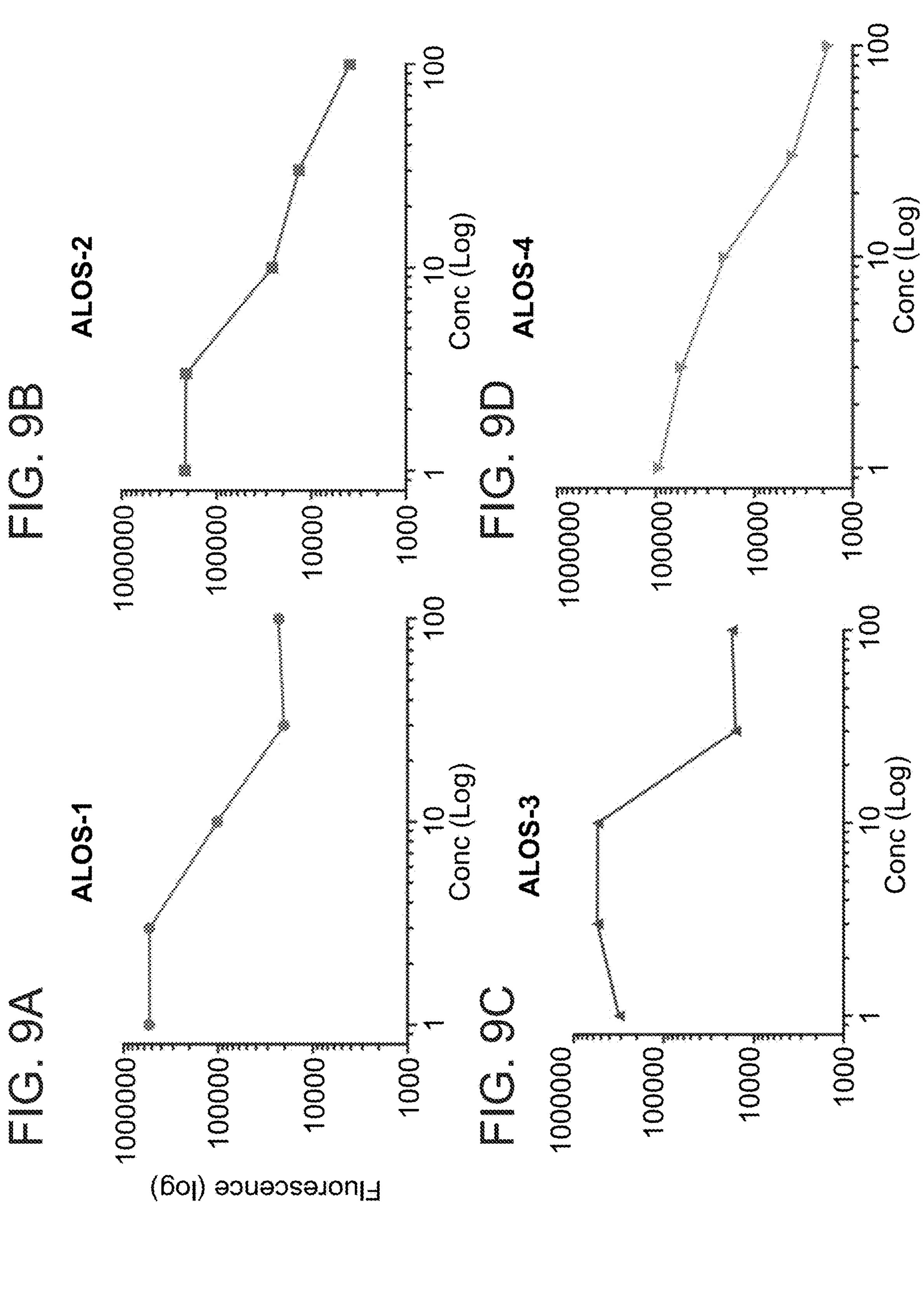
FIGS. 9A-9D are graphs illustrating competitive homologous binding analysis. 10 μM of FITC labeled ALOS peptides were incubated with different concentrations of unlabeled ALOS peptides on wells pre-coated with purified Integrin $\alpha v\beta 3$. Fluorescence was measured using Enspire Plate reader (PerkinElmer). The plots were built using nonlinear regression one site homologous binding plot analysis (GraphPad Prism).
Figure 10:
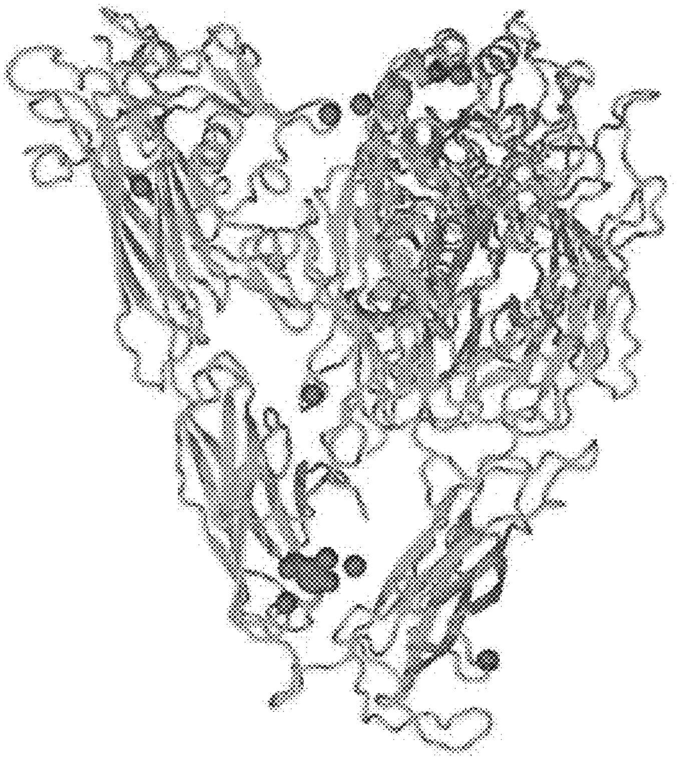
FIG. 10 is a model which depicts docking simulations of the cyclic peptide ALOS-4 to $\alpha v\beta 3$ integrin. 10000 docking simulations were performed using the ROSSETA software. The top 20 best results are presented as spheres corresponding to the center of mass of the cyclic peptide. The cluster of spheres (marked with black arrow) indicates the most likely binding site of the peptide.

In this experiment binding of ALOS peptides to integrin were compared to scrambled FITC-labeled 7 amino acids peptides. Fluorescence of ALOS peptides was positively correlated with concentration of FITC-labeled peptides when tested on wells coated with αvβ3. In contrast, scrambled peptides showed lack of binding affinity to integrin (FIG. 8). This study further demonstrates the unique nature of ALOS peptides to bind αvβ3.

Competitive Homologous Binding Analysis

Homologous competition binding experiments were performed using labeled and unlabeled ligands bearing identical affinities for the receptors. The competition was performed at varying concentrations of unlabeled ALOS peptides against fixed concentrations of FITC-labeled ALOS peptide. As demonstrated on FIGS. 9A-D, fluorescence density was correlated with concentration of unlabeled peptide.

Example 4

Binding Experiments to αvβ5, αvβ3 and α5β1

Figure 11:
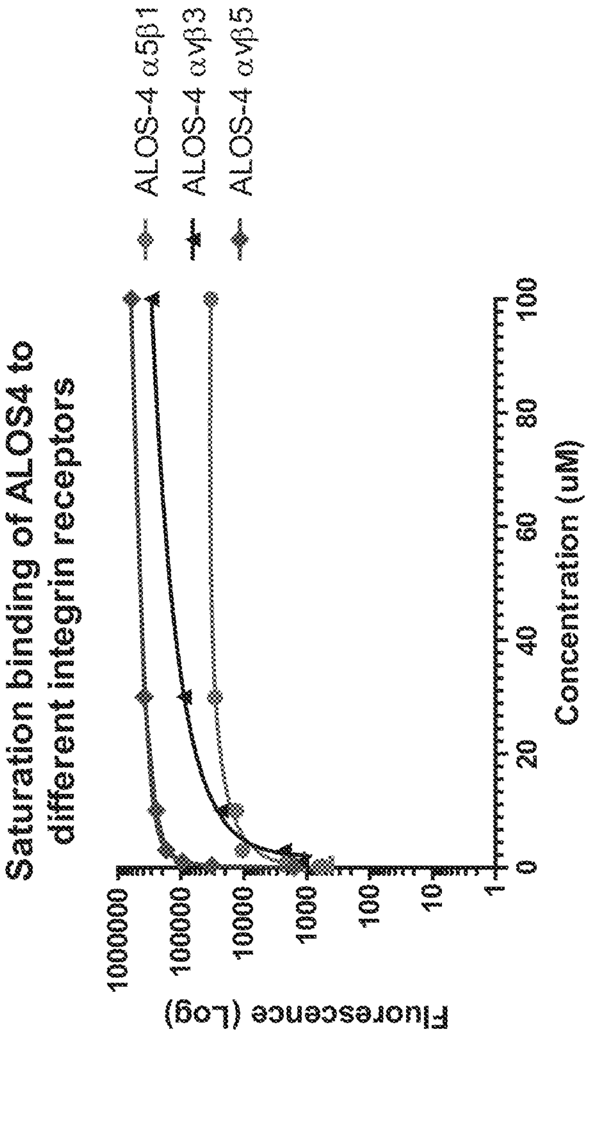
FIG. 11 is a graph comparing the binding capability of Fluorescein (FITC)—labeled ALOS4 peptide to purified Integrins $\alpha v\beta 3$ $\alpha v\beta 5$ and $\alpha 5\beta 1$ compared to $\alpha v\beta 5$, collagen (CG) and bovine serum albumin (BSA). Peptides (concentrations 100 μM, 30 μM, 10 μM, 1 μM) were added to integrin pre-coated wells for 30 min. The fluorescence was measured using Enspire plate reader (PerkinElmer). The plots were built using nonlinear regression analysis (GraphPad Prism).
Figures 12A, 12B, 12C, 12D:
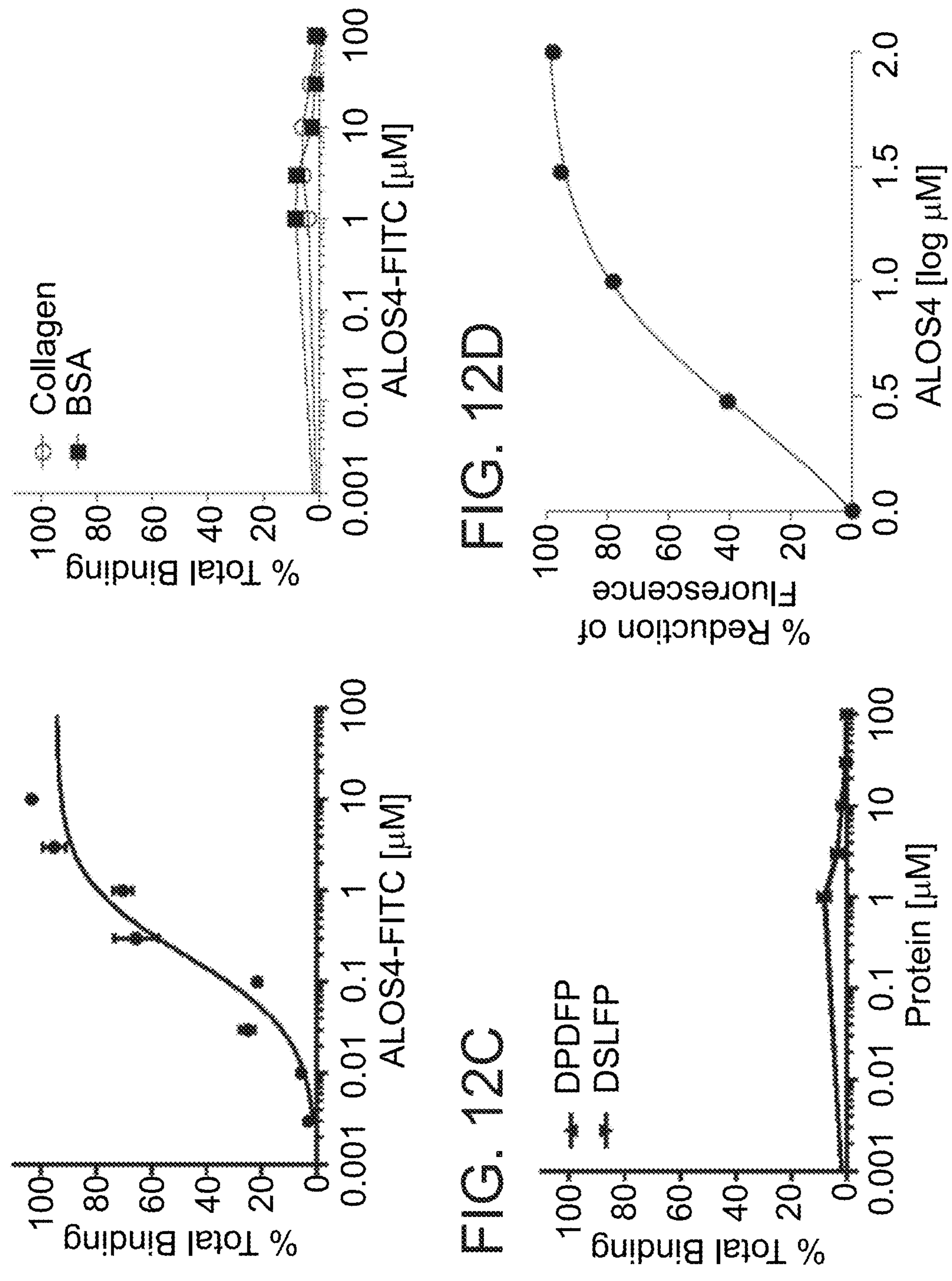
FIGS. 12A-12D illustrate selective binding of ALOS4 to αvβ3. (A) ALOS4-FITC binding in wells pre-coated with integrin αvβ3. ALOS4 binding to αvβ3: Kd=0.192±0.038 μM. (B) ALOS4-FITC binding in wells coated with collagen or BSA. (C) Binding of random, FTIC-labeled cyclic peptide controls (DPDFP and DSLFP) in wells pre-coated with integrin αvβ3. (D) Competitive homologous binding of ALOS4 to αvβ3 integrin. 10 μM of ALOS4-FITC peptide was incubated with different concentrations of unlabeled ALOS4 on wells pre-coated with αvβ3. Kd=2.55±1.22 μM. Data are expressed as percent reduction of maximal fluorescence signal.

The effect of binding affinity of ALOS4 to other members of integrin family of receptors was evaluated. As demonstrated in FIG. 11, ALOS4 binds to αvβ5 and α5131 integrins. As demonstrated in FIGS. 12A-D, ALOS4 binds to αvβ5 and α5131 integrins.

Example 5

Effect of ALOS4 on Melanoma Cells

A. Subcutaneous Melanoma Mouse Model

Figure 13:
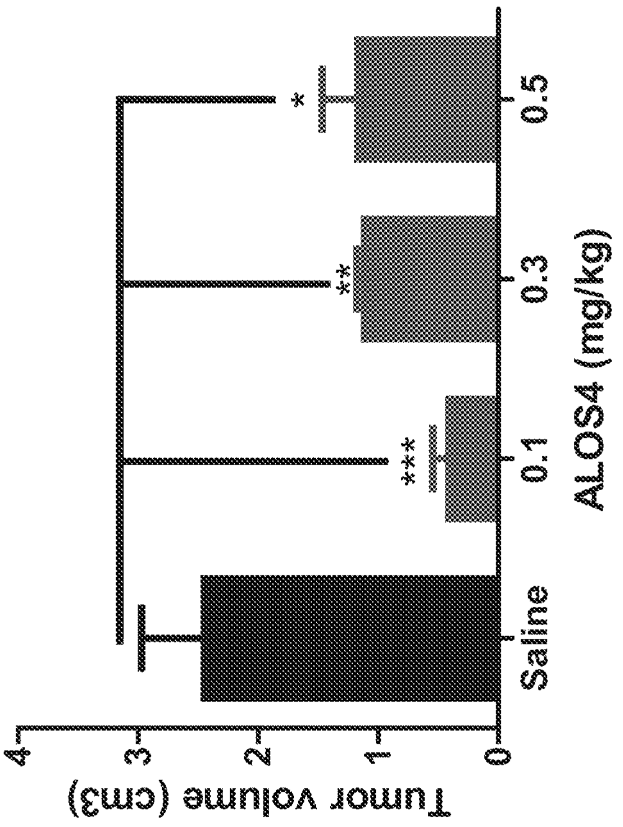
FIG. 13 is a graph showing the effect of ALOS4 administration on tumor volume in the subcutaneous melanoma mouse model. $5\times10^5$ cells/mouse was injected subcutaneously to each C57BL/6 mice. ALOS4 (0.1, 0.3, 0.5 mg/kg) was administered next day after cells inoculation, daily (during working week days). Tumors volume was measured on day 23. n=6-7 animals in each group. Statistical analysis was done using one-way ANOVA, followed by Bonferroni post-hoc correction.
Figure 14:
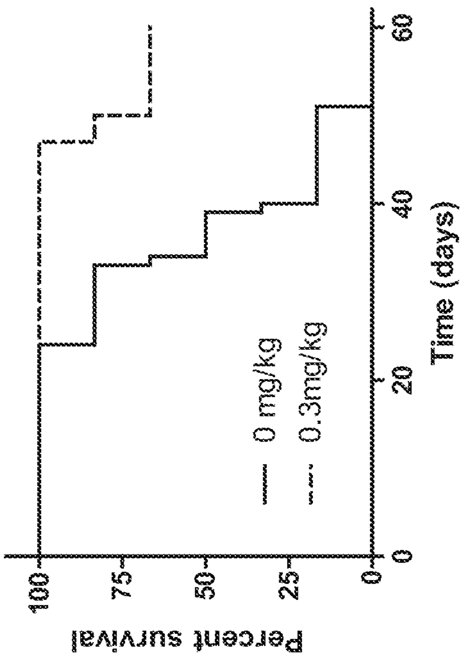
FIG. 14 is a graph illustrating that ALOS4 increases survival rate in subcutaneous model mice. C57BL/6 mice were inoculated subcutaneously with B16F10 cells and treated i.p. with ALOS4 0.3 mg/kg 5 days a week, n=6 mice.

The subcutaneous model is used for the evaluation of treatment in many tumor models, including melanoma. Upon subcutaneous injection, B16F10 cells form a palpable tumor in 5 to 10 days. When allowed to grow larger, the tumors often become necrotic in the center and begin to ulcerate or bleed. In this experiment it was found that ALOS4 markedly reduced tumor volume of experimental mice (FIG. 13). Furthermore, i.p. injection of ALOS4 (0.3 mg/kg 5 days a week, n=6) was shown to increase survival rate in C57BL/6 mice which were inoculated subcutaneously with B16F10 cells (FIG. 14).

B. In Vitro Model of Metastasizing Cancer Cells

Figure 15B:
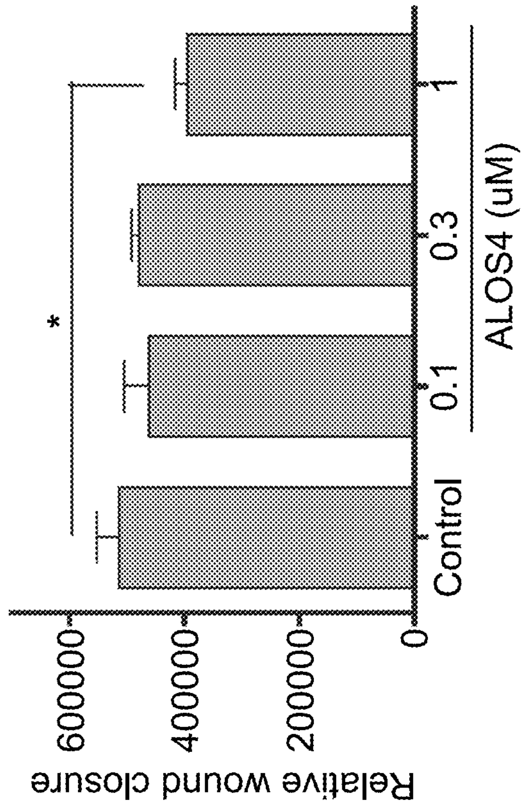
FIGS. 15A-15B illustrates the effect of ALOS4 on migration rate in melanoma cells. B16F10 cells were treated with ALOS4 for 48 h at 0.1, 0.3 and 1 μM. The cells were wounded (T=0) and incubated at 37° C. for 8 hours (T=8). Migration rate was determined using ImageJ software. A. Relative wound closure (ΔsT0-T8). B. Live-imaging microscopy picture at time 0 and 8, demonstrated wound closure. (t-test: *, p<0.05).
Figure 15A:
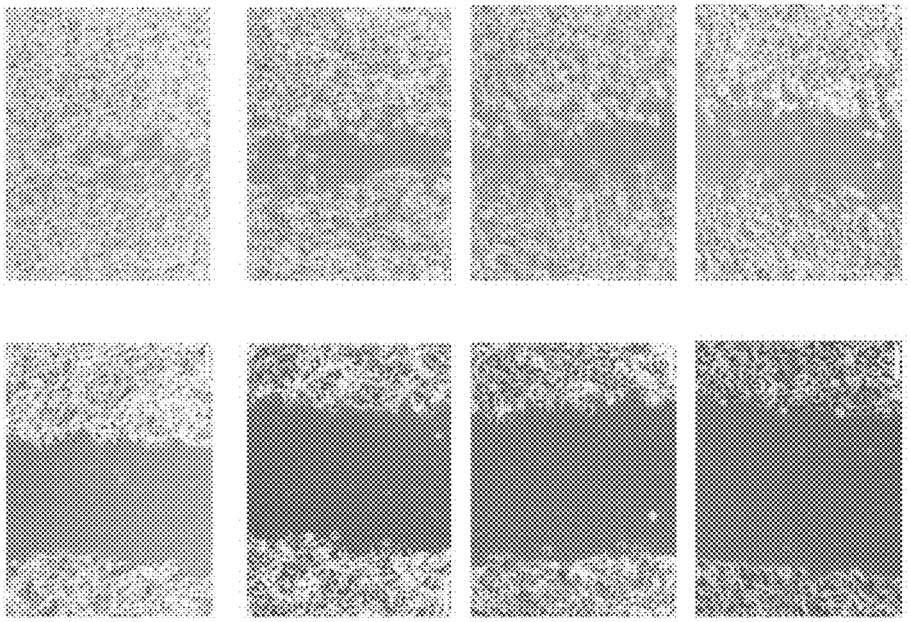

Confluent cell cultures were "scratched" (time 0) and the wound site imaged. 8 hours after wounding, the culture was reimaged and the difference between open areas in the view-frame from time 0 were calculated. A small, ALOS4 concentration-dependent effect on cell migration rate (approximately 80% of control at 1 uM) was observed—see FIGS. 15A-B.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

REFERENCES

1. Ginsberg M H, Integrin activation, BMB Rep. 2014 December; 47(12):655-9.
2. Janet A. Askari, Patrick A. Buckley, A. Paul Mould and Martin J. Humphries. Linking integrin conformation to function Journal of Cell Science 122 (2): 165-170, 2009.
3. Desgrosellier J S, Cheresh D A. Integrins in cancer: biological implications and therapeutic opportunities. Nat Rev Cancer. 2010; 10:9-22.
4. Guo W and Giancotti F G. Integrin signaling during tumor progression. Nature Reviews, Molecular Cell Biology, 5: 816-26, 2004.
5. Rathinam R and Alahari S K. Important role of integrins in the cancer biology. Cancer Metastasis Rev. 2010.
6. Alam N, Goel H L, Zarif M J, Butterfield J E, Perkins H M, Sansoucy B G, Sawyer T K and Languino L R. The Integrin Growth Factor Receptor Duet. Cell. Physiol. 213: 649-653, 2007.
7. Carter A. Integrins as Target: First Phase III Trial Launches, but Questions Remain. JNCI Vol. 102, Issue 10 I: 675-677, 2010.
8. Hersey P, Sosman J, O'Day S, Richards J, Bedikian A, Gonzalez R, Sharfman W, Weber R, Logan T, Buzoianu M, Hammershaimb L, Kirkwood J M. A randomized phase 2 study of etaracizumab, a monoclonal antibody against integrin alpha(v)beta(3), + or − dacarbazine in patients with stage IV metastatic melanoma. Cancer. 116(6):1526-34, 2010.

What is claimed is:

1. An isolated peptide consisting of an amino acid sequence selected from the group consisting of SEQ ID NOs: 5 and 12-14.

2. A pharmaceutical composition comprising as the active agent the peptide of claim 1, and a pharmaceutically acceptable carrier.

3. A method of treating a disease or condition associated with serotonin transport or a αVβ3 activity in a subject in need thereof, the method comprising administering to the subject a therapeutically effective amount of a peptide comprising an amino acid sequence selected from the group consisting of SEQ ID NOs: 12-14, thereby treating the disease.

4. The method of claim 3, wherein said peptide is capable of binding to αVβ3 integrin.

5. The method of claim 3, wherein said peptide is a cyclic peptide.

6. The method of claim 5, wherein the N terminal amino acid and the C terminal amino acids of said peptides are cysteines.

7. The method of claim 3, wherein said peptide is no more than 50 amino acids in length.

8. The method of claim 3, wherein said peptide is no more than 20 amino acids in length.

9. The method of claim 3, wherein the disease or condition is selected from the group consisting of depression, anxiety, phobia, addiction, aggressiveness, impulsiveness, panic, eating, sleep and psychotic disorder and obsessive-compulsive and female sexual dysfunctions.

10. The method of claim 3, wherein the disease is cancer.

11. The method of claim 10, wherein said cancer is a metastasized cancer.

12. The method of claim 10, wherein said cancer is selected from the group consisting of melanoma, ovarian cancer and cervical cancer.

13. A method of treating a behavioral disease or condition associated with serotonin transport or a αVβ3 activity in a subject in need thereof, the method comprising administering to the subject a therapeutically effective amount of a peptide comprising an amino acid sequence selected from the group consisting of SEQ ID NOs: 11 or 15, thereby treating the disease, wherein said subject is suffering from a disease or condition selected from the group consisting of depression, anxiety, phobia, addiction, aggressiveness, impulsiveness, panic, eating, sleep and psychotic disorder and obsessive-compulsive and female sexual dysfunctions.

* * * * *